US012644085B2

(12) United States Patent
Mukesh et al.

(10) Patent No.: US 12,644,085 B2
(45) Date of Patent: Jun. 2, 2026

(54) NEURAL LATTICE DEVICE FOR CHARACTERIZATION OF NEURON BEHAVIOR

(71) Applicant: INTERNATIONAL BUSINESS MACHINES CORPORATION, Armonk, NY (US)

(72) Inventors: Sagarika Mukesh, Albany, NY (US); Steven Holmes, Red Hook, NY (US); John S. Werner, Fishkill, NY (US); Benjamin Hardy Wunsch, Mt. Kisco, NY (US); Arkadiy O. Tsfasman, Wappingers Falls, NY (US)

(73) Assignee: International Business Machines Corporation, Armonk, NY (US)

( * ) Notice: Subject to any disclaimer, the term of this patent is extended or adjusted under 35 U.S.C. 154(b) by 685 days.

(21) Appl. No.: 17/933,509

(22) Filed: Sep. 20, 2022

(65) Prior Publication Data

US 2024/0101943 A1 Mar. 28, 2024

(51) Int. Cl.
| | |
|---|---|
| *C12M 3/06* | (2006.01) |
| *B81B 1/00* | (2006.01) |
| *B81C 1/00* | (2006.01) |
| *C12M 1/00* | (2006.01) |
| *G01N 33/50* | (2006.01) |

(52) U.S. Cl.
CPC ............. *C12M 23/16* (2013.01); *B81B 1/002* (2013.01); *B81C 1/00047* (2013.01); *C12M 23/58* (2013.01); *G01N 33/5058* (2013.01); *B81B 2201/058* (2013.01); *B81B 2201/06* (2013.01)

(58) Field of Classification Search
CPC ...... C12M 23/16; C12M 23/58; C12M 21/08; B81B 1/002; B81B 2201/058; B81B 2201/06; B81C 1/00047; G01N 33/5058
See application file for complete search history.

(56) References Cited

U.S. PATENT DOCUMENTS

| | | | |
|---|---|---|---|
| 2004/0224002 A1 | 11/2004 | Fishman et al. | |
| 2004/0230270 A1 | 11/2004 | Huie et al. | |
| 2007/0111353 A1* | 5/2007 | McCaskill ........... | H05K 1/0272 438/42 |

(Continued)

FOREIGN PATENT DOCUMENTS

| | | |
|---|---|---|
| EP | 3117828 B1 | 2/2020 |
| WO | 2008004010 A2 | 1/2008 |

OTHER PUBLICATIONS

Gordon, "General Overview of Neuronal Cell Culture", Neuronal Cell Culture: Methods and Protocols, Methods in Molecular Biology, vol. 1078, Chapter 1, 2013; 8p.

(Continued)

*Primary Examiner* — John McGuirk

(74) *Attorney, Agent, or Firm* — CANTOR COLBURN LLP; Samuel Waldbaum

(57) ABSTRACT

A neural lattice device includes a substrate having formed therein one or more wells and one or more supply ducts. A channel network includes one or more channels configured to establish fluid communication among the at least one well and the at least one supply duct. A reservoir is coupled to the substrate and configured to hold a fluid, and a cover is disposed against an upper surface of the substrate and configured to hermetically seal the wells, the supply ducts and the channel network.

9 Claims, 35 Drawing Sheets

(56) References Cited

U.S. PATENT DOCUMENTS

| | | |
|---|---|---|
| 2014/0113366 A1 | 4/2014 | Dahan et al. |
| 2019/0339257 A1 | 11/2019 | Miklas et al. |
| 2020/0299629 A1 | 9/2020 | Cesare et al. |
| 2020/0380343 A1 | 12/2020 | Holmes et al. |
| 2021/0403853 A1* | 12/2021 | Ludlam .................. C12M 23/20 |

OTHER PUBLICATIONS

James, "Aligned Microcontact Printing of Micrometer-Scale Poly-L-Lysine Structures for Controlled Growth of Cultured Neurons on Planar Microelectrode Arrays", IEEE Transactions on Biomedical Engineering, vol. 47, No. 1, Jan. 2000, 5p.

Teixeira, "Recent Developments in Microfluidic Technologies for Central Nervous System Targeted Studies", MDPI Pharmaceutics, 2020; 3p.

* cited by examiner

1

NEURAL LATTICE DEVICE FOR CHARACTERIZATION OF NEURON BEHAVIOR

BACKGROUND

The present invention generally relates to fabrication methods and resulting structures for semiconductor devices, and more specifically, to fabrication methods and a resulting neural lattice device for characterization of neuron behavior.

Biological neural structures are often highly complex in nature and are often difficult to effectively characterize and physically model. For example, in a highly complex neural network such as a brain, it is often difficult to isolate, characterize and utilize specific neurons due to the sheer density of biological neural material. Instead, the biological signals obtained by sensors or other devices that are inserted into the biological neural structures typically comprise noisy signals that include information associated with more than one neuron or even millions of neurons. Synthetic neural networks have been utilized in semiconductor memory devices to mimic biological neural structures. However, synthetic neural networks do not provide the same level of functionality that may be found in biological neural structures.

SUMMARY

According to a non-limiting method, a neural lattice device includes a substrate having formed therein one or more wells and one or more supply ducts. A channel network includes one or more channels configured to establish fluid communication among the at least one well and the at least one supply duct. A reservoir is coupled to the substrate and configured to hold a fluid, and a cover is disposed against an upper surface of the substrate and configured to hermetically seal the wells, the supply ducts and the channel network.

According to another non-limiting embodiment, a method of fabricating a neural lattice device comprises forming at least one well in a substrate and forming at least one supply duct in the substrate. The well is configured to hold a biological neuron and the supply duct is configured to receive a nutrient fluid. The method further comprises forming in the substrate a channel network including one or more channels configured to establish fluid communication among the at least one well and the at least one supply duct, and coupling a reservoir to the substrate, the reservoir configured to hold a fluid. The method further comprises disposing a cover against an upper surface of the substrate and configured to hermetically seal the at least one well, the at least one supply duct, and the channel network.

Other embodiments of the present invention implement features of the above-described devices/structures in methods and/or implement features of the methods in devices/structures.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings presented herein.

Figure 1A:
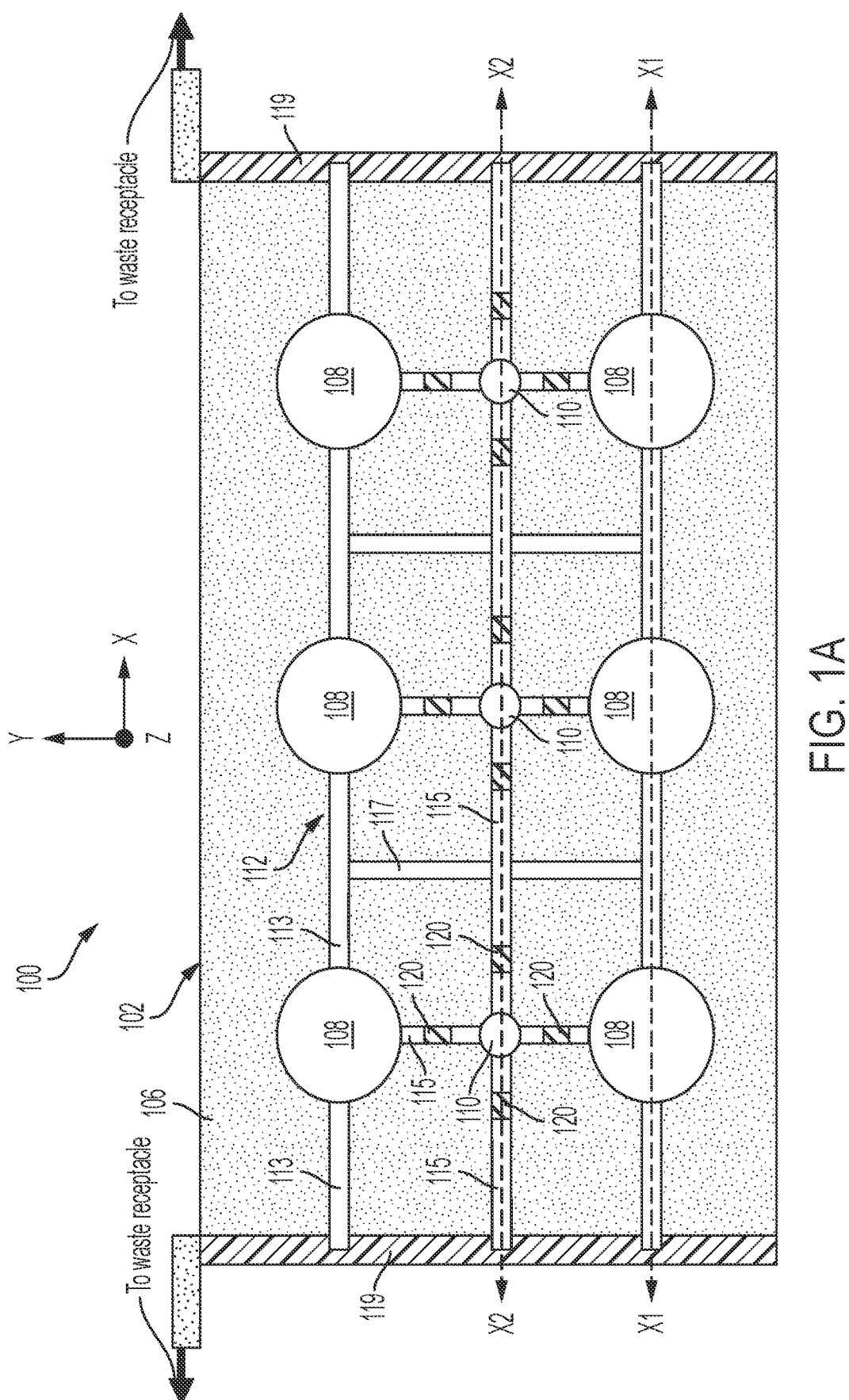
Figure 1B:
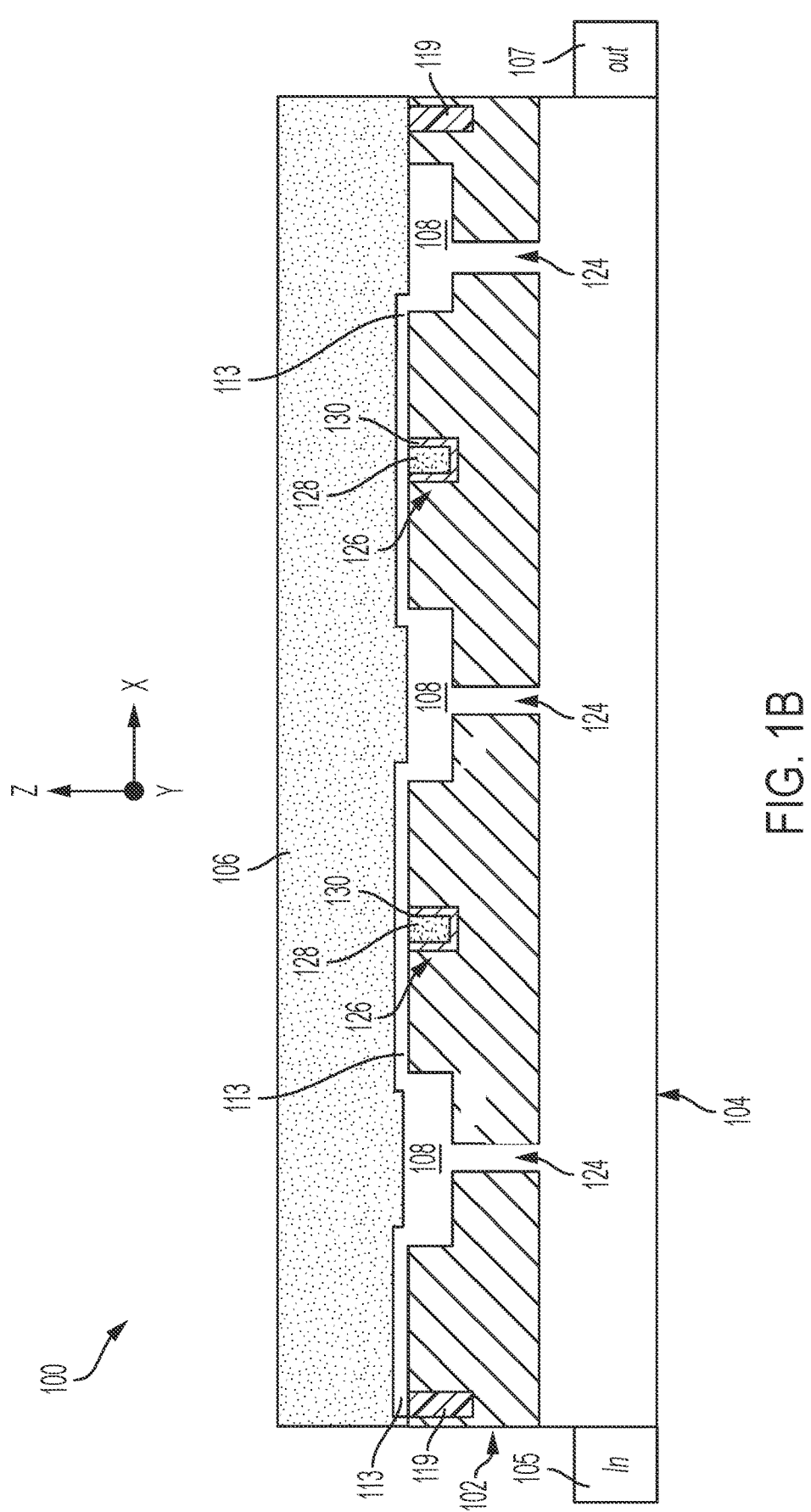
Figure 1C:
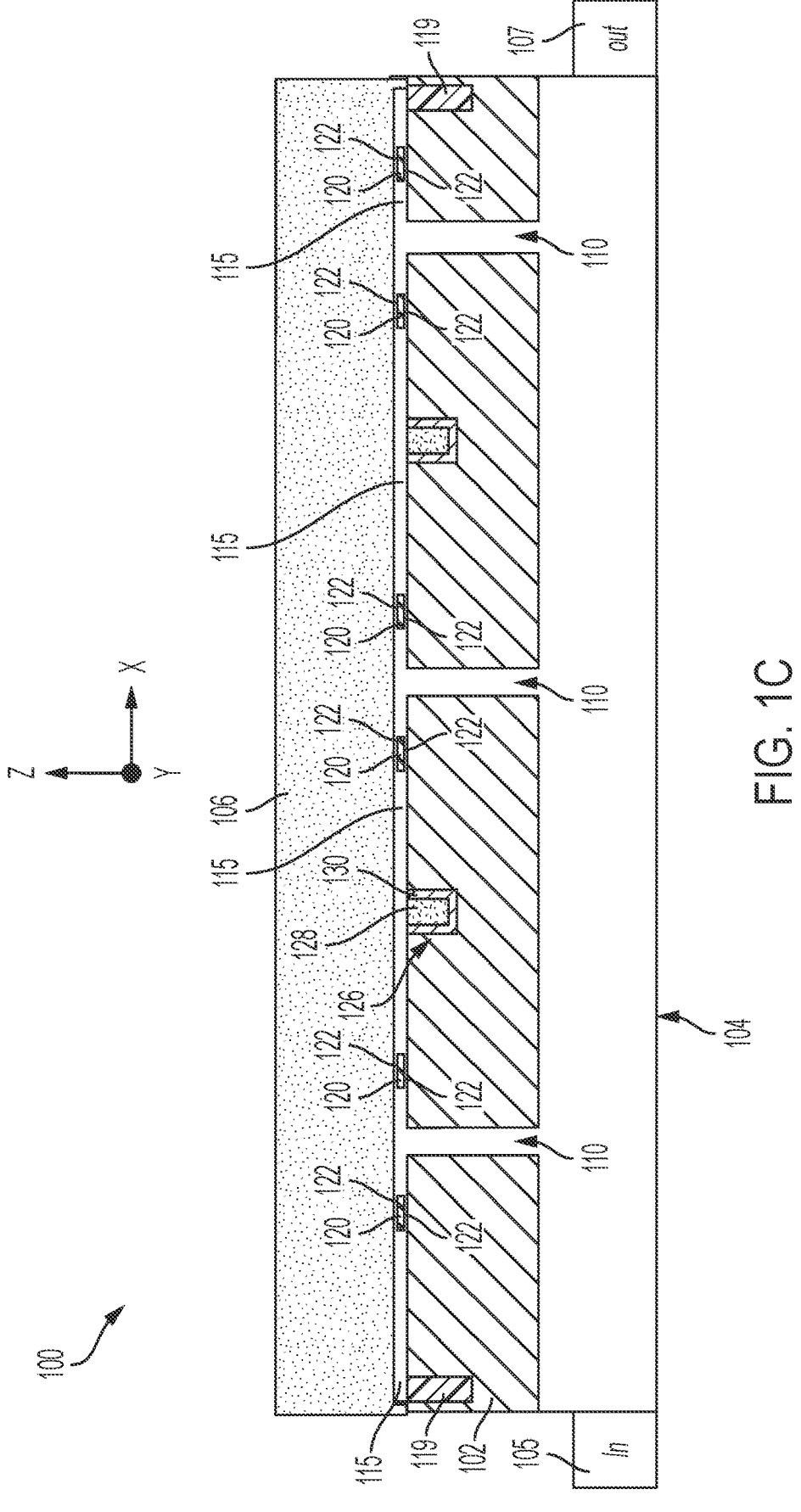

FIG. 1A is a top view of a neural lattice device according to a non-limiting embodiment of the invention;

FIG. 1B is a cross-section view illustrating the neural lattice device shown in FIG. 1A in a first orientation taken along line X-X; and FIG. 1C is a cross-section view illustrating the neural lattice device shown in FIG. 1A in a second orientation taken along line Y-Y.

Figure 2:
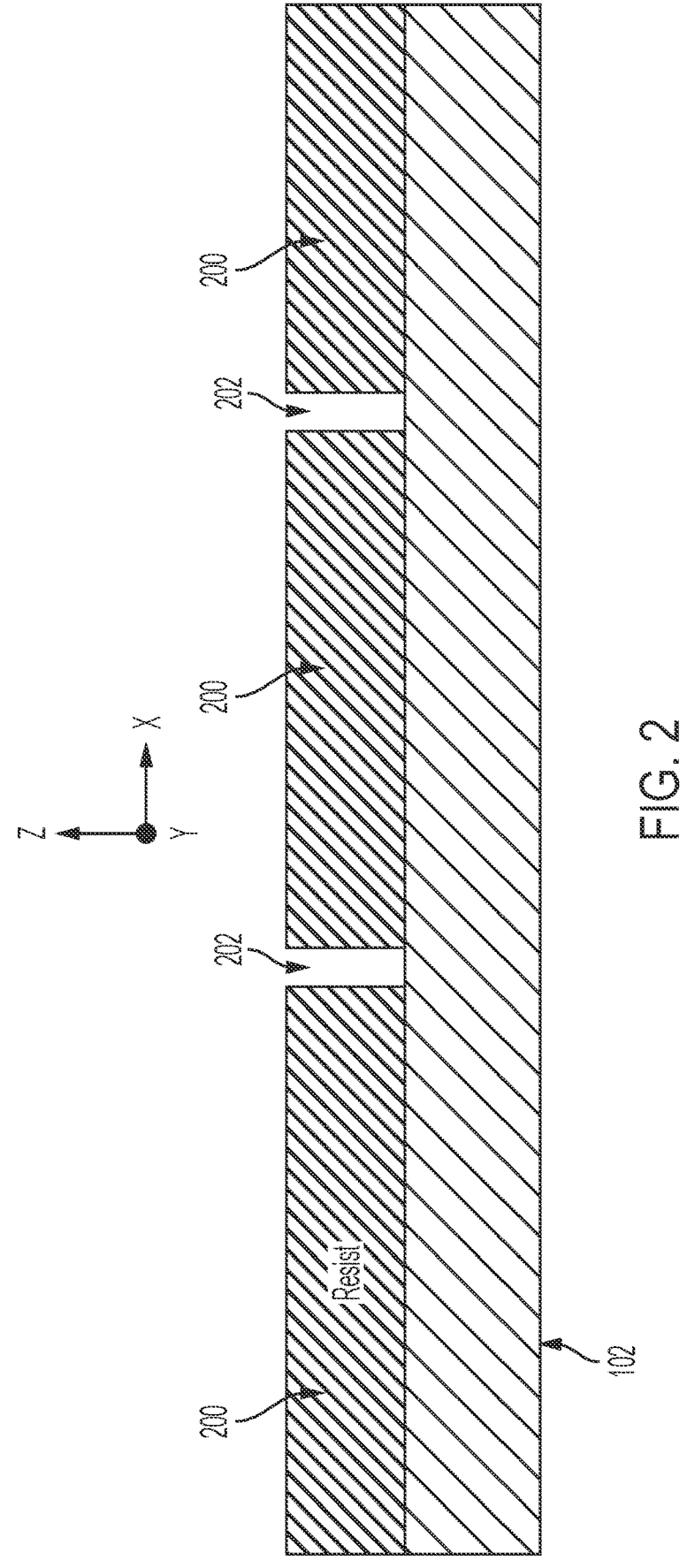
Figure 3:
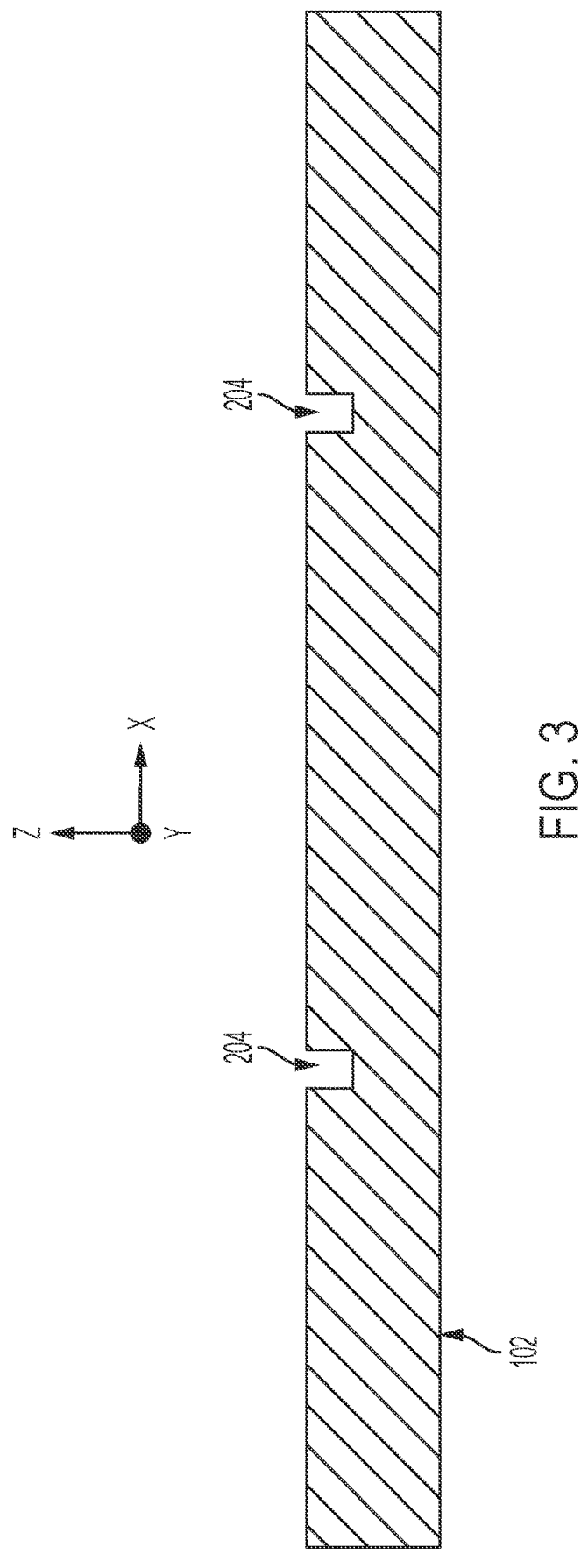
Figure 4:
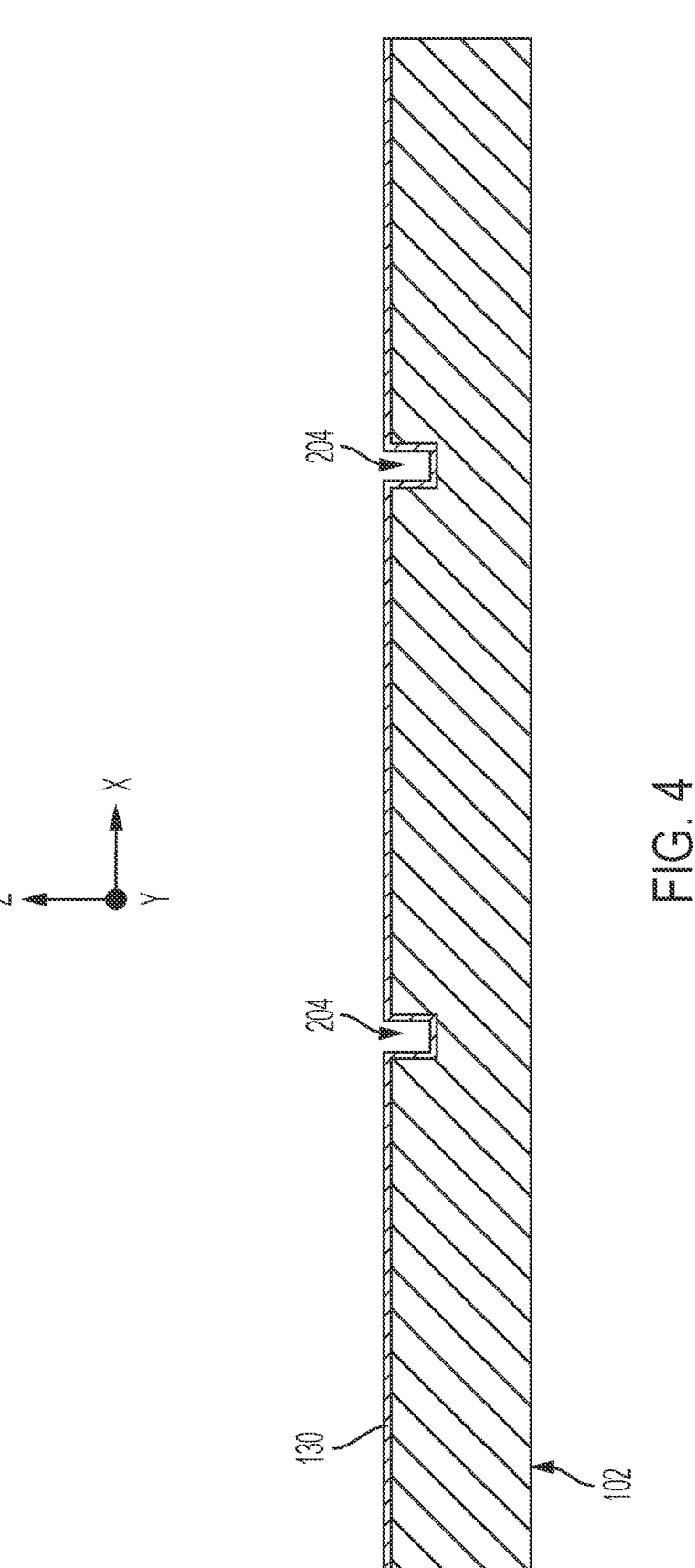
Figure 5:
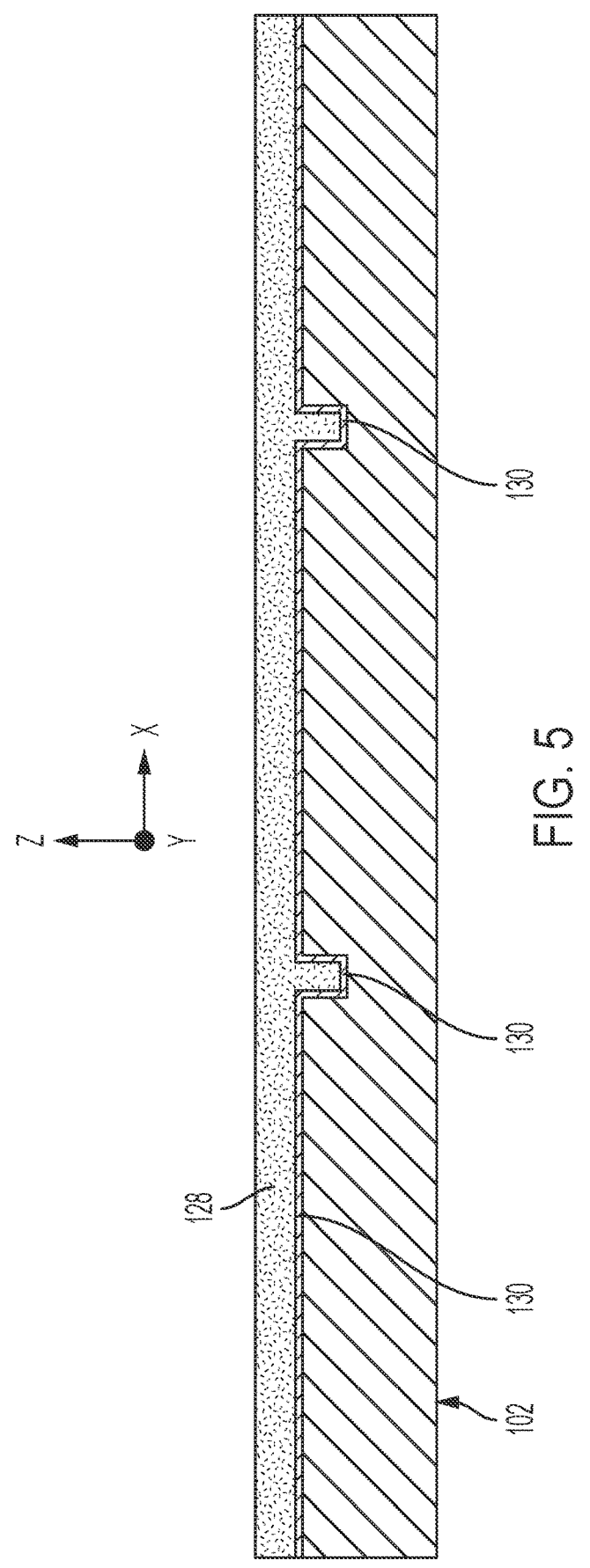
Figure 6:
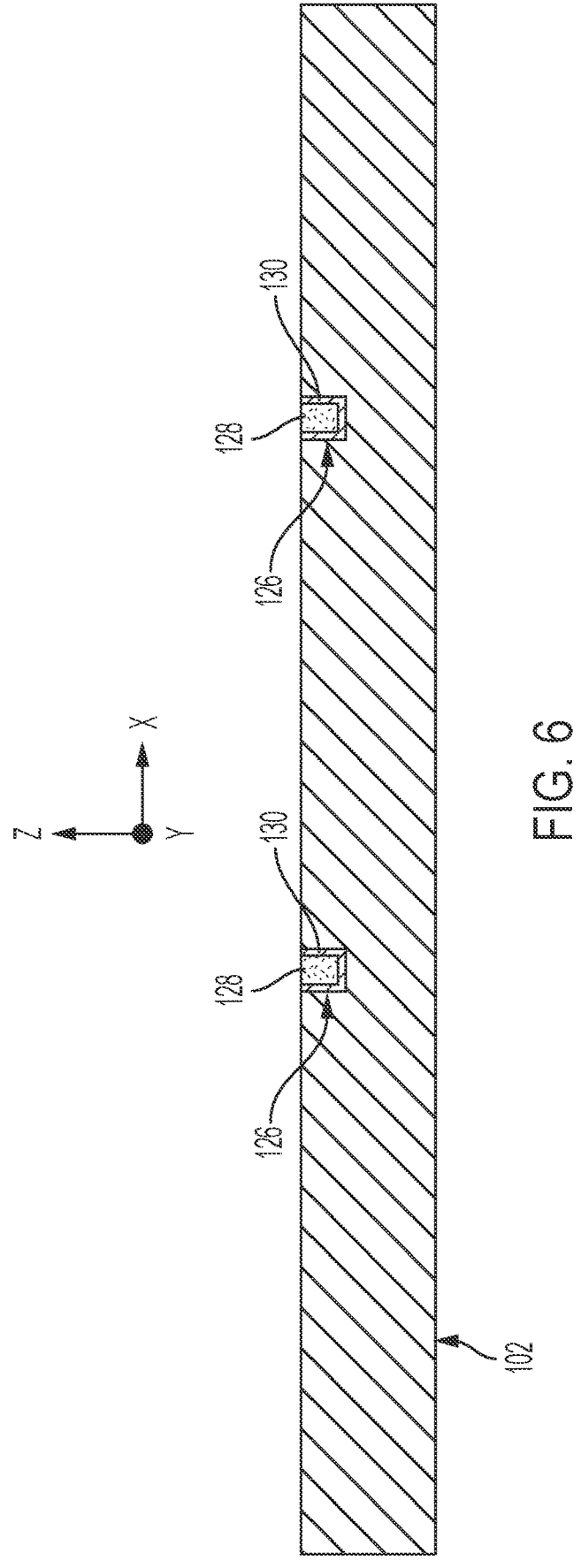
Figure 7:
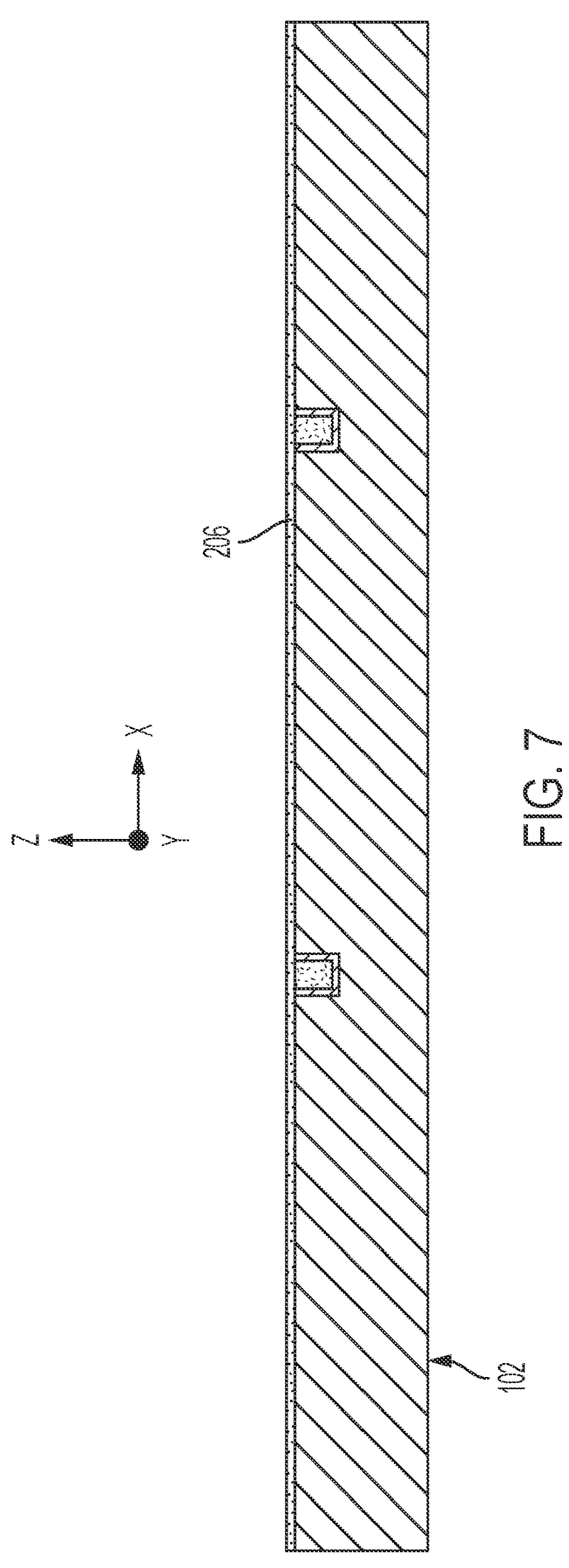
Figure 8A:
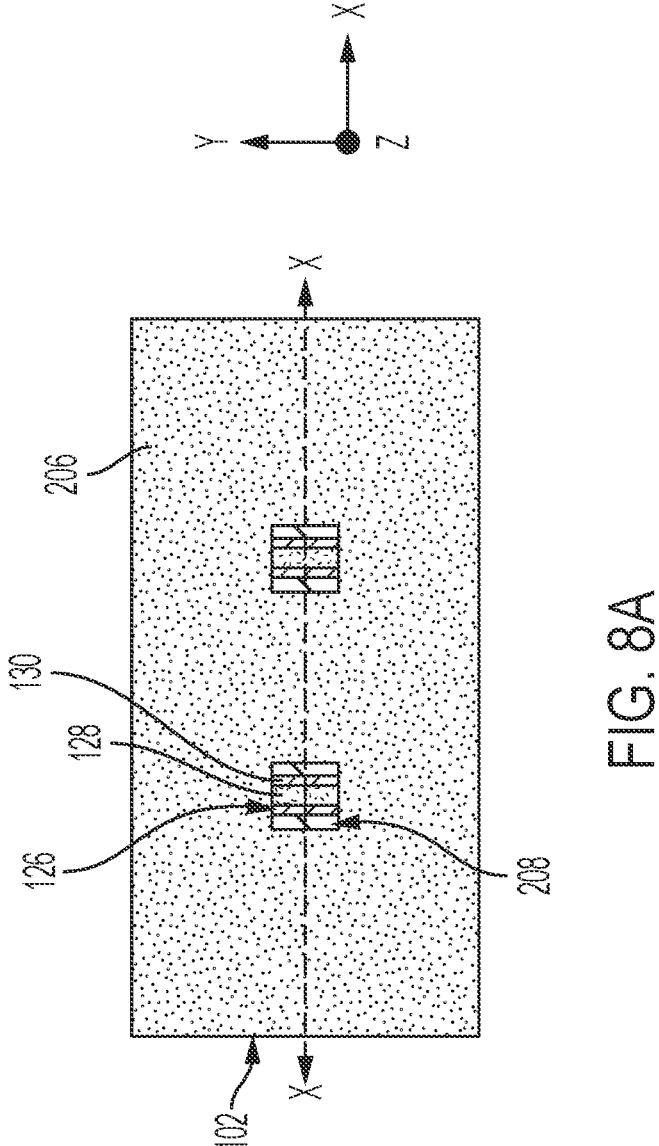
Figure 8B:
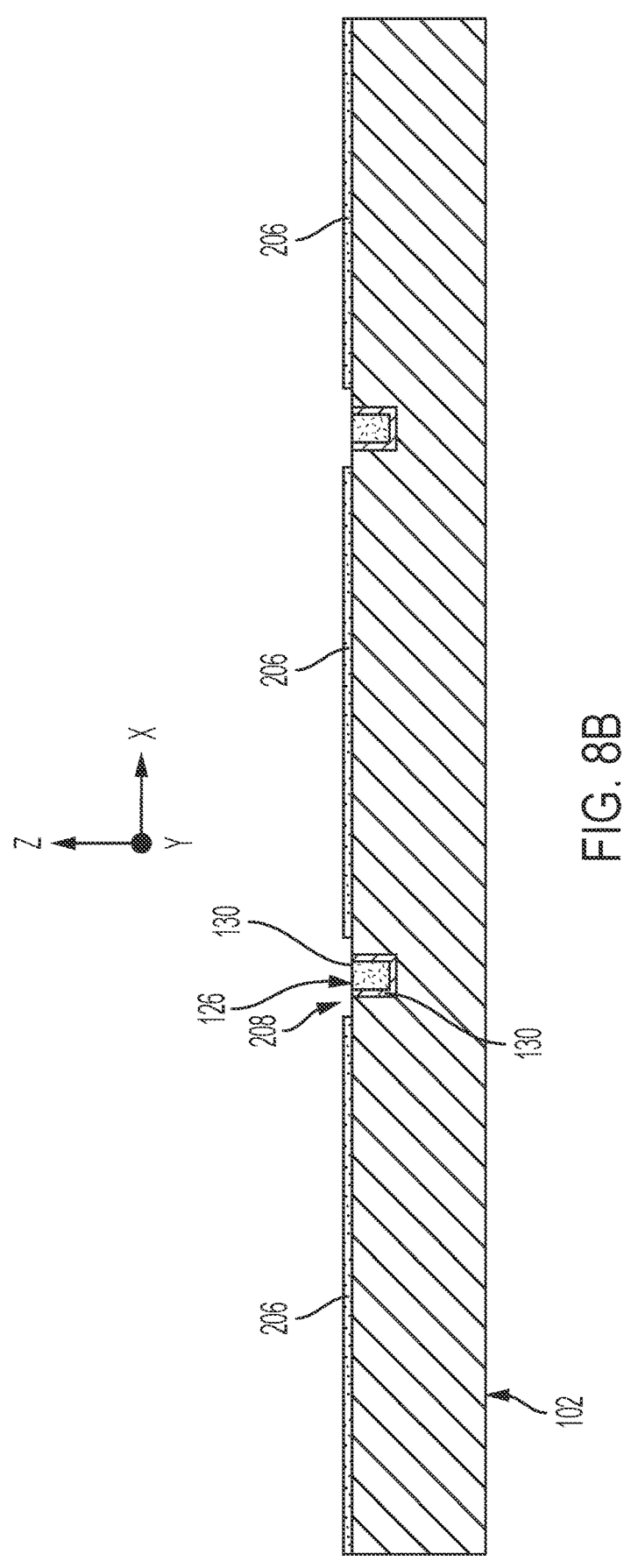
Figure 9A:
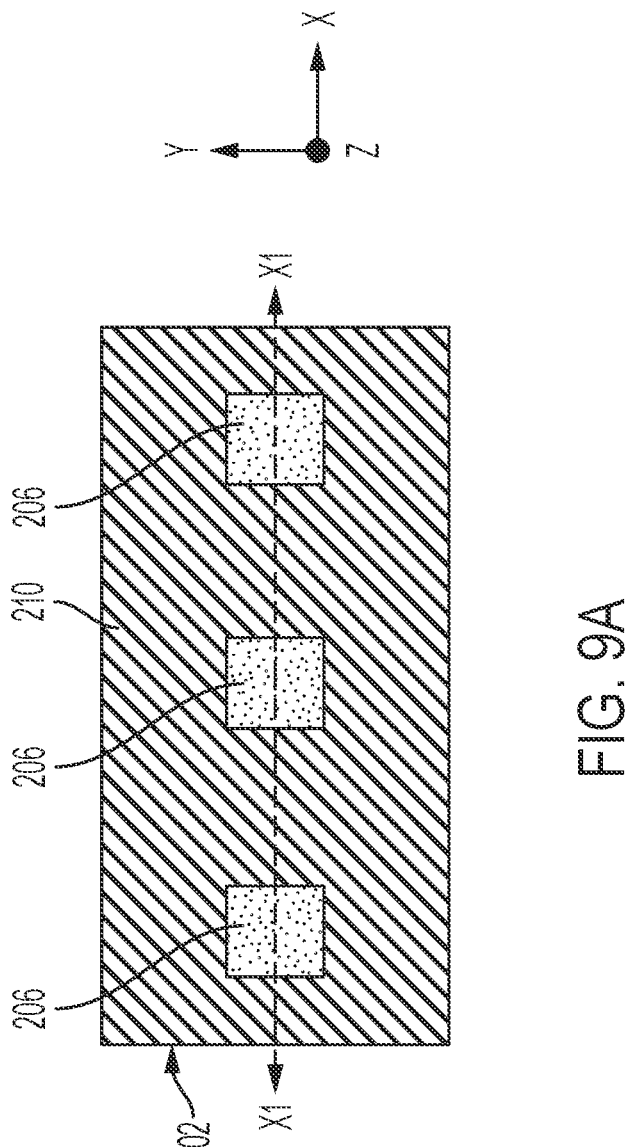
Figure 9B:
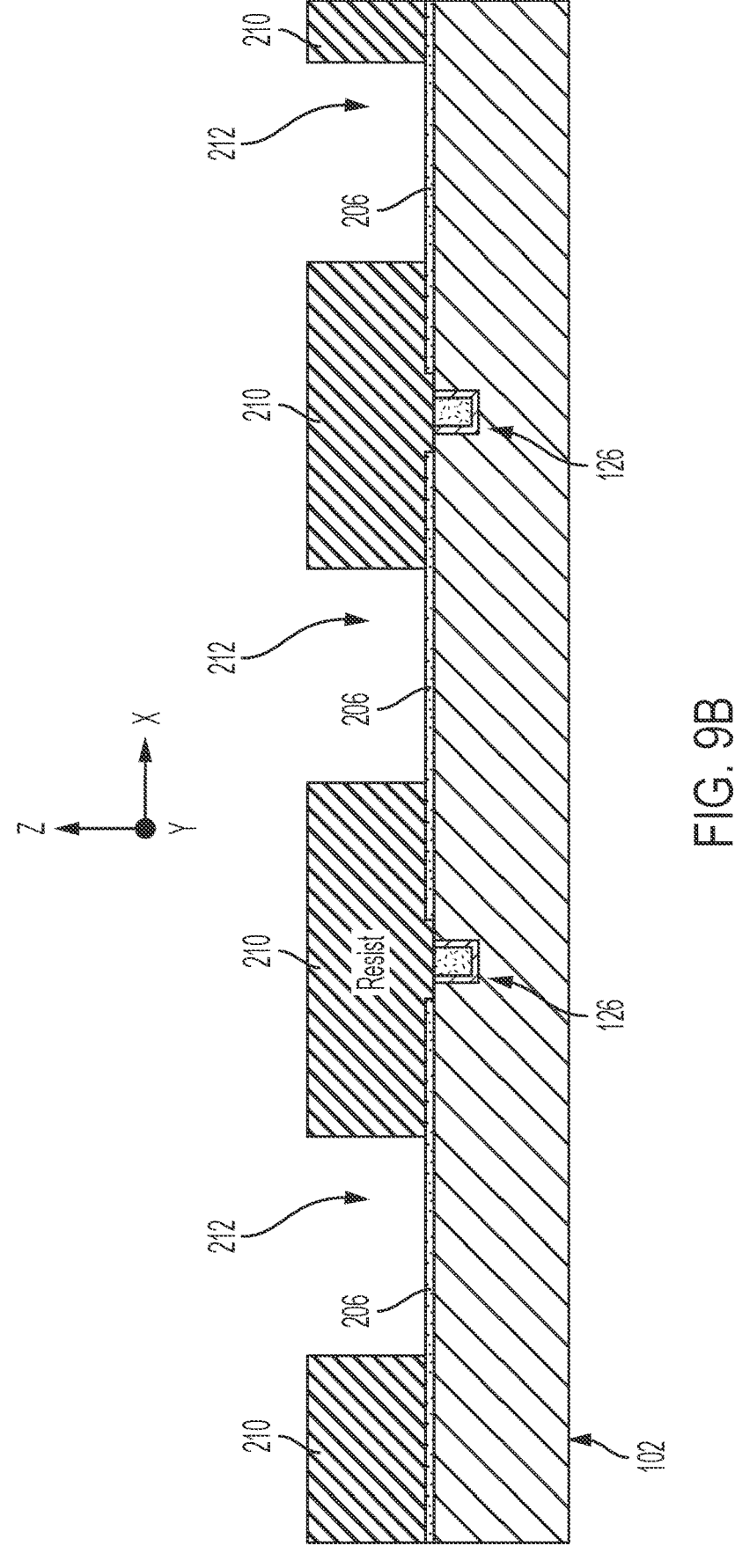
Figure 10A:
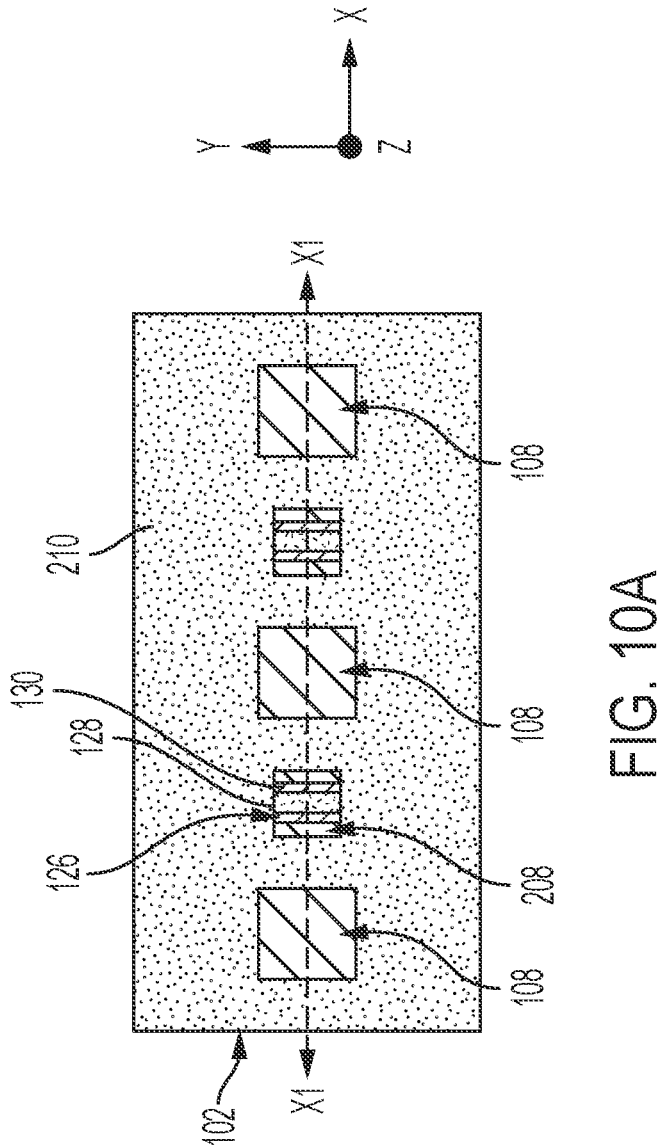
Figure 10B:
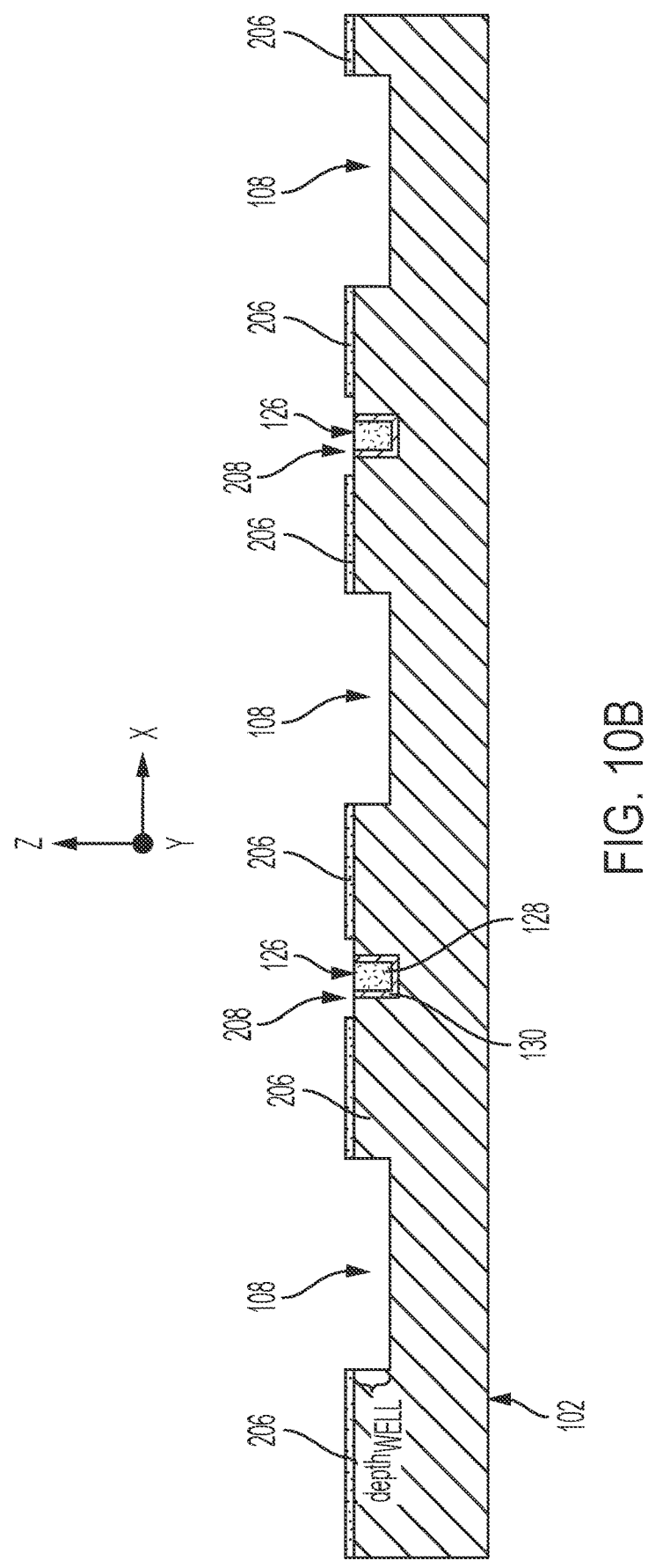
Figure 11A:
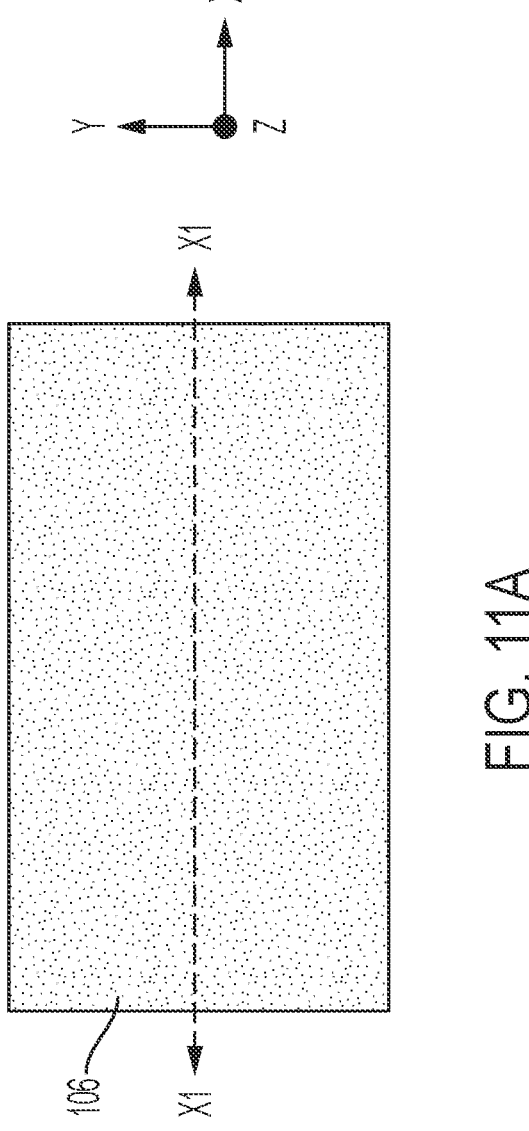
Figure 11B:
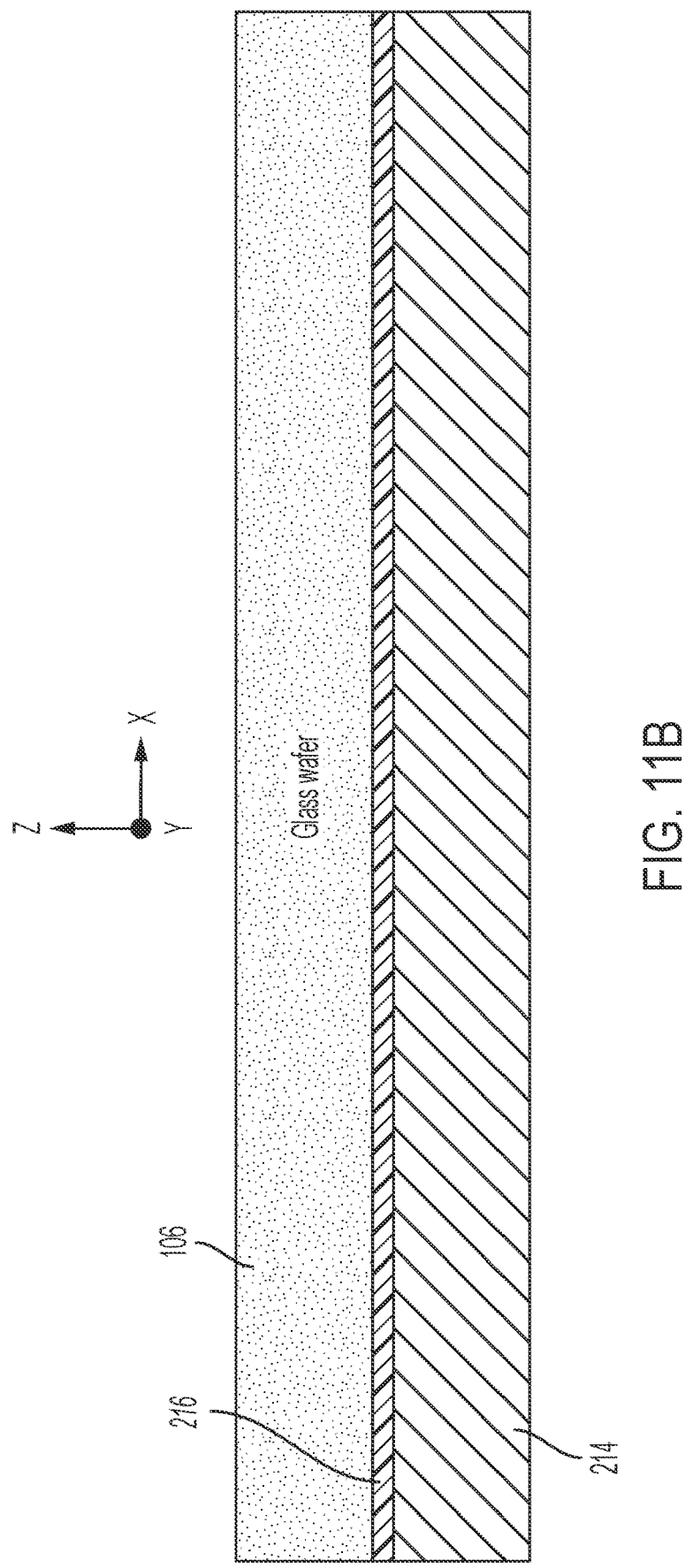
Figure 12A:
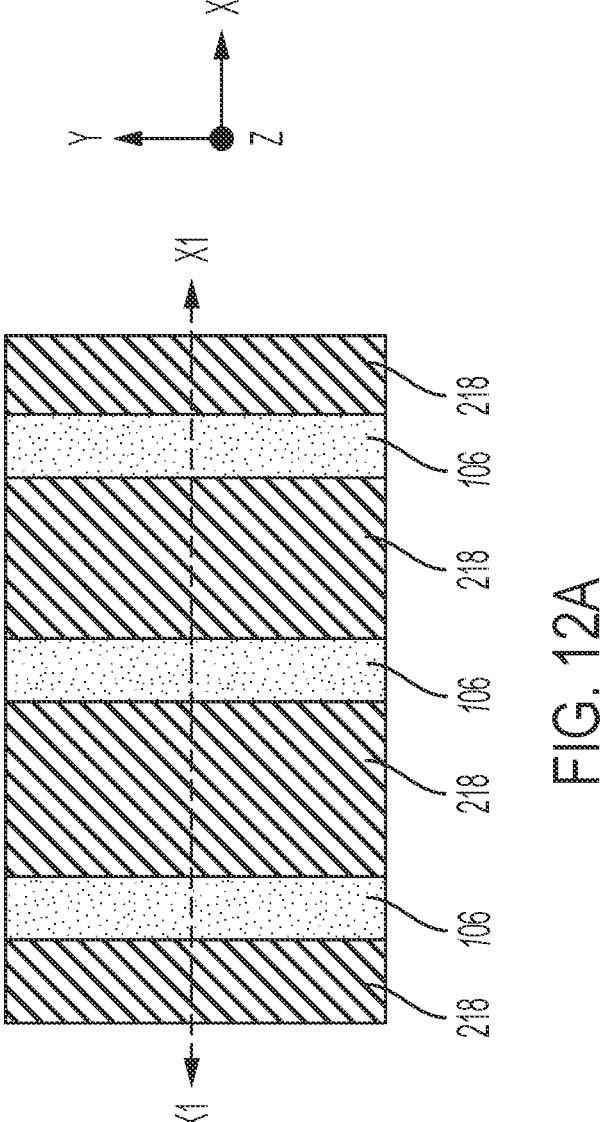
Figure 12B:
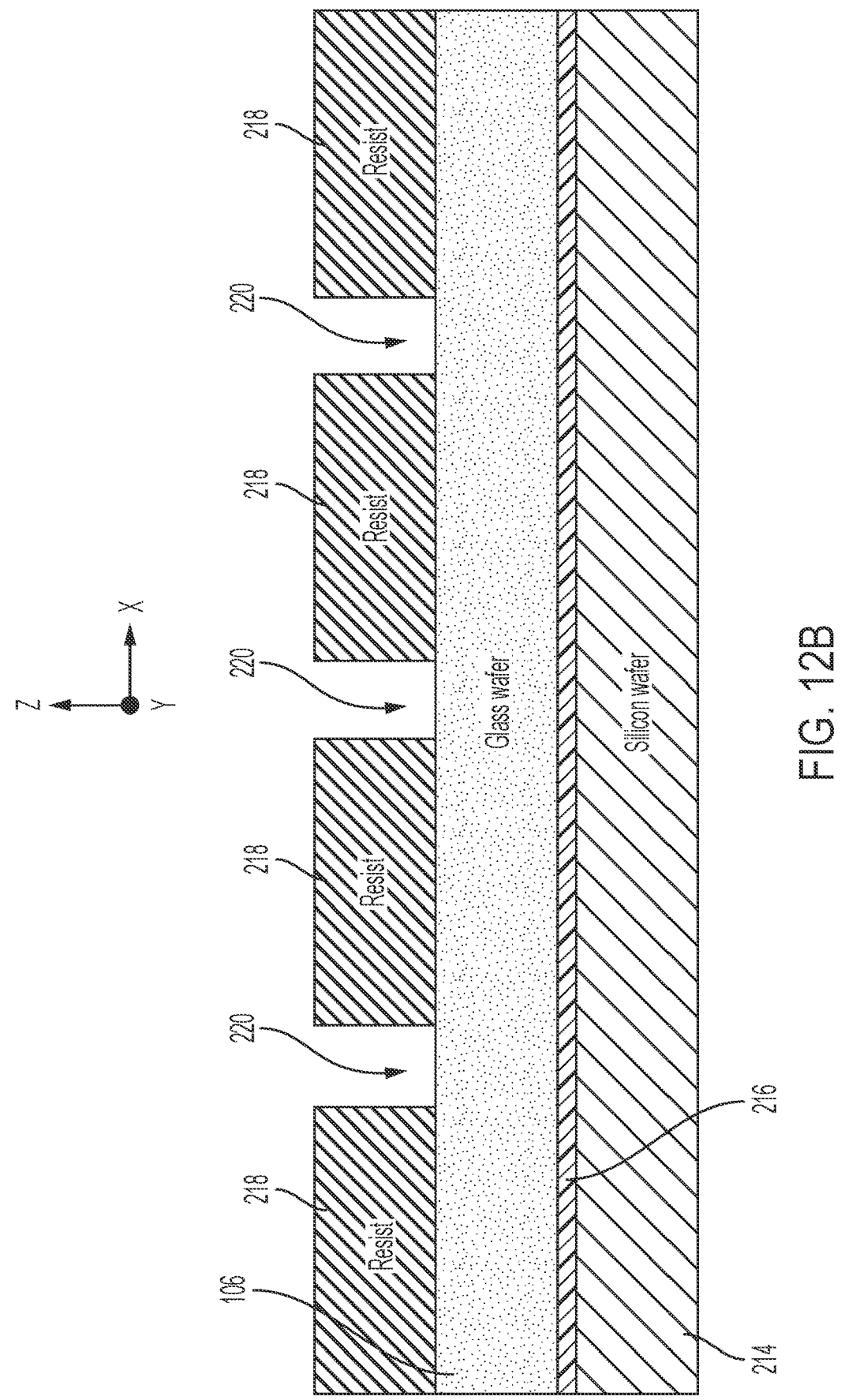
Figure 13A:
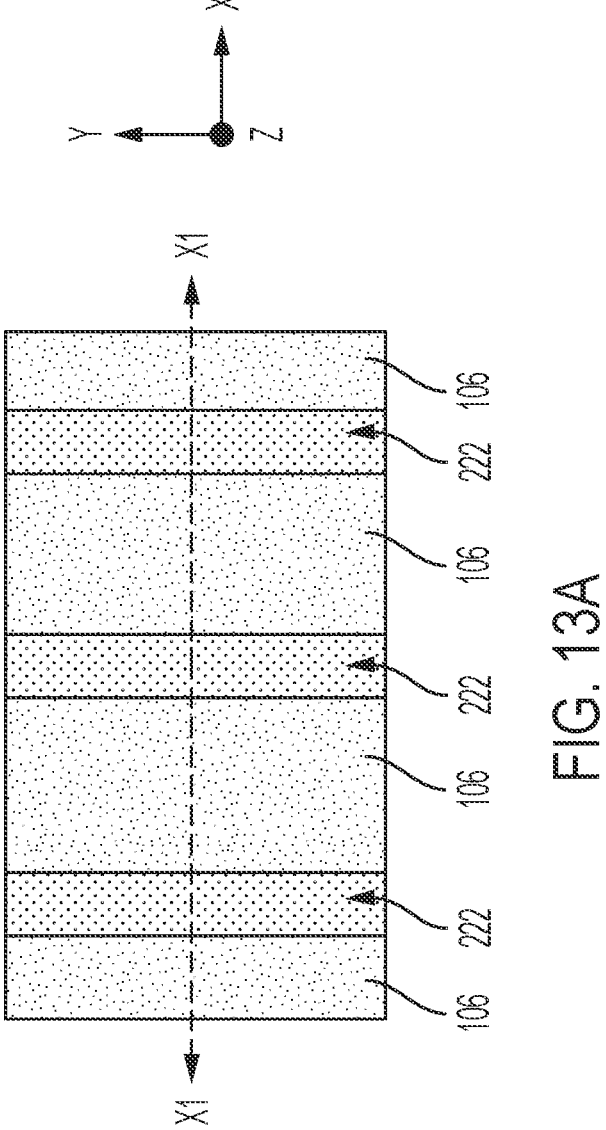
Figure 13B:
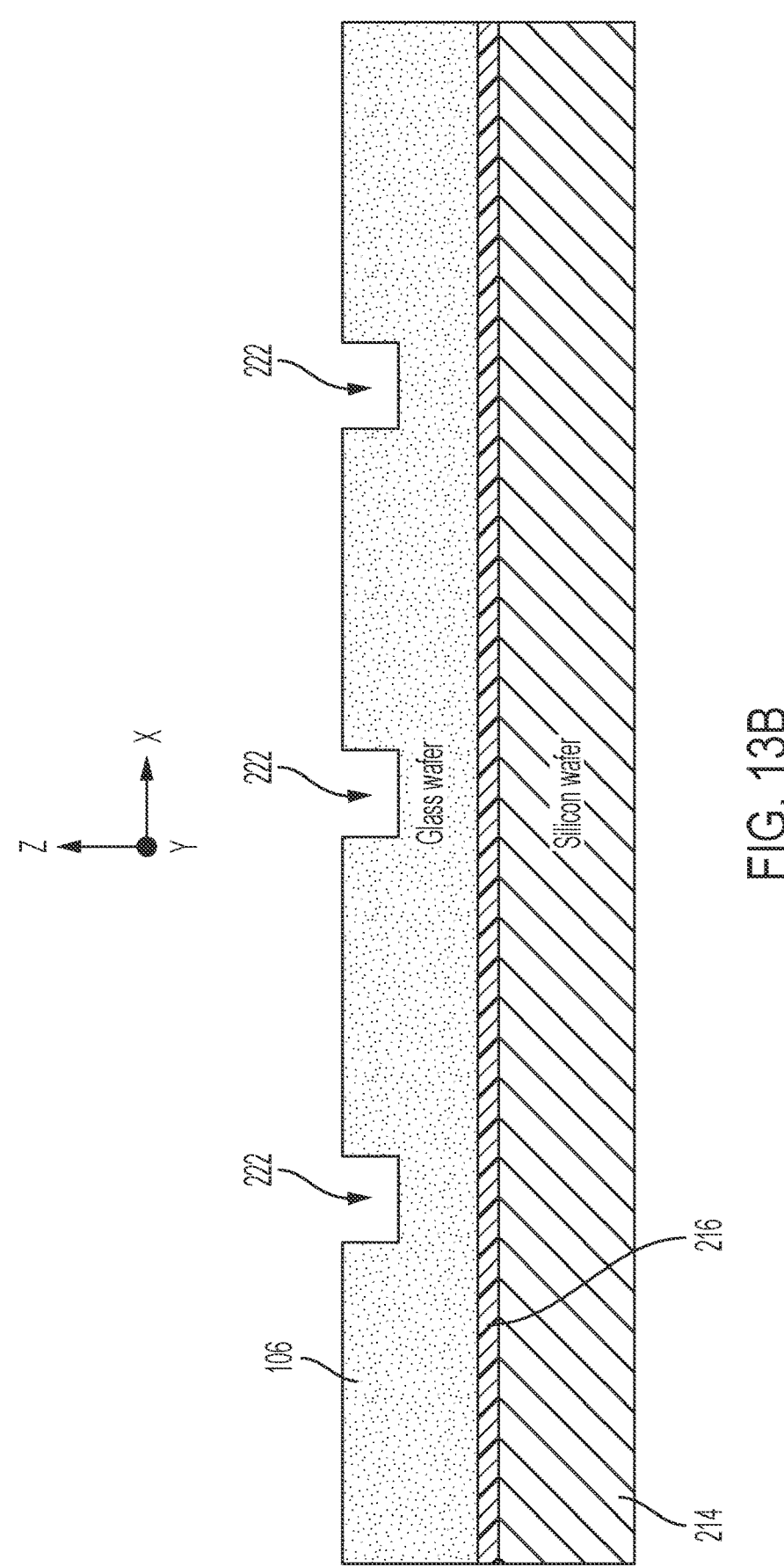
Figure 14A:
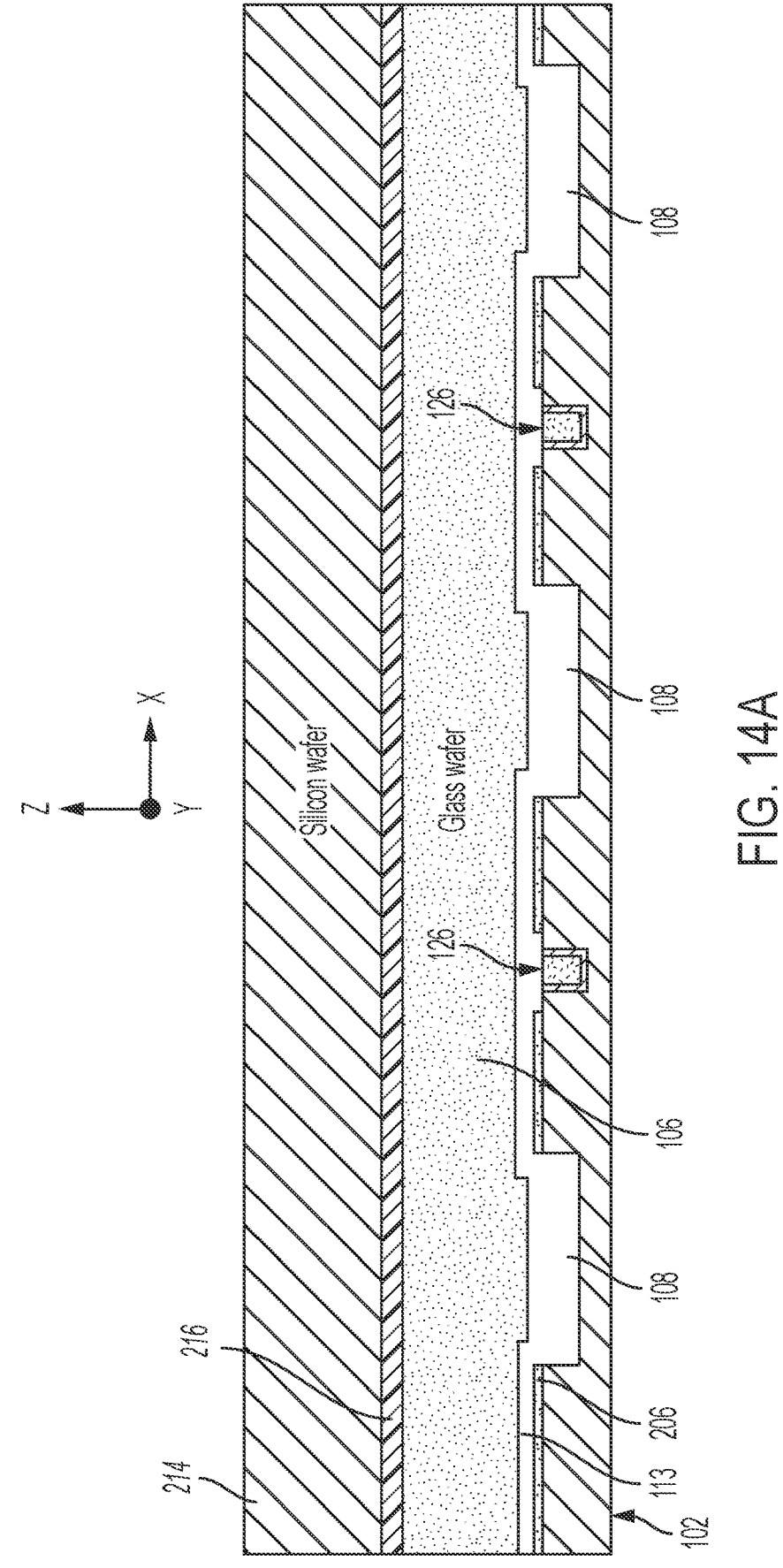
Figure 14B:
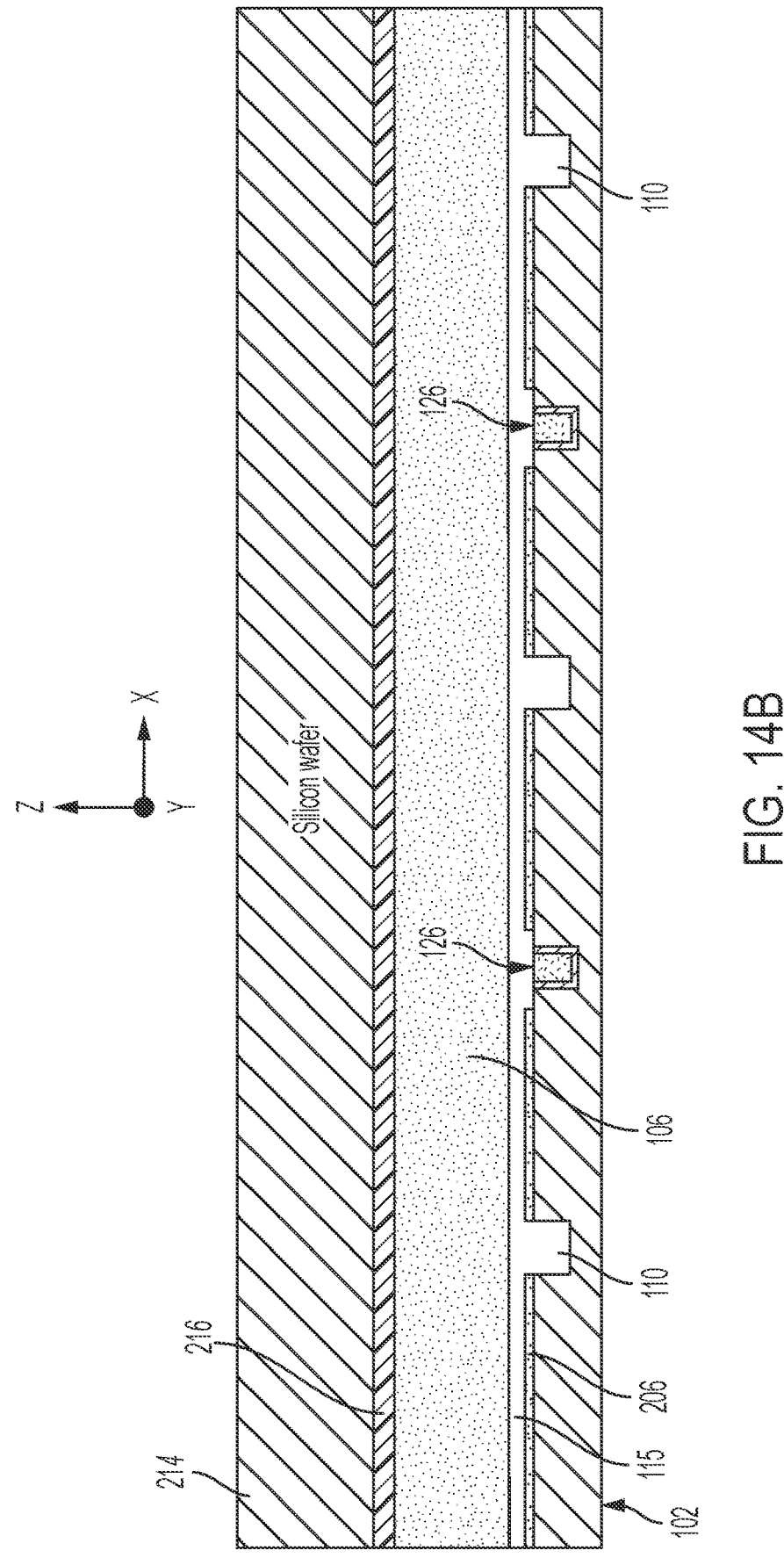
Figure 15A:
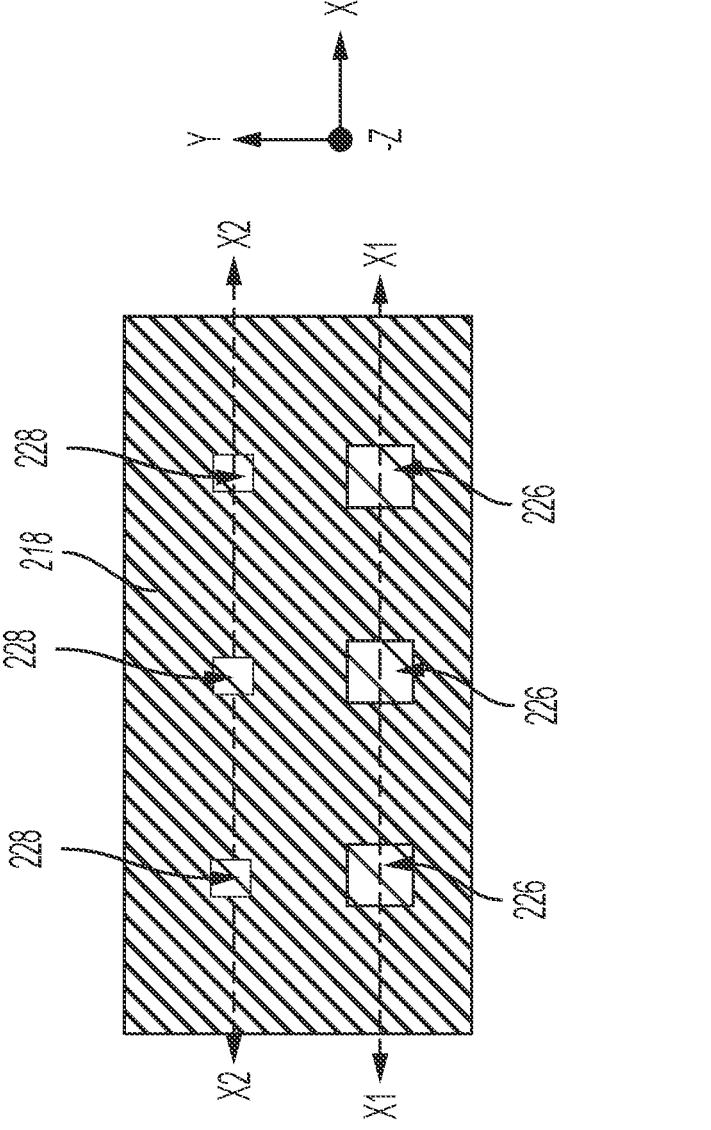
Figure 15B:
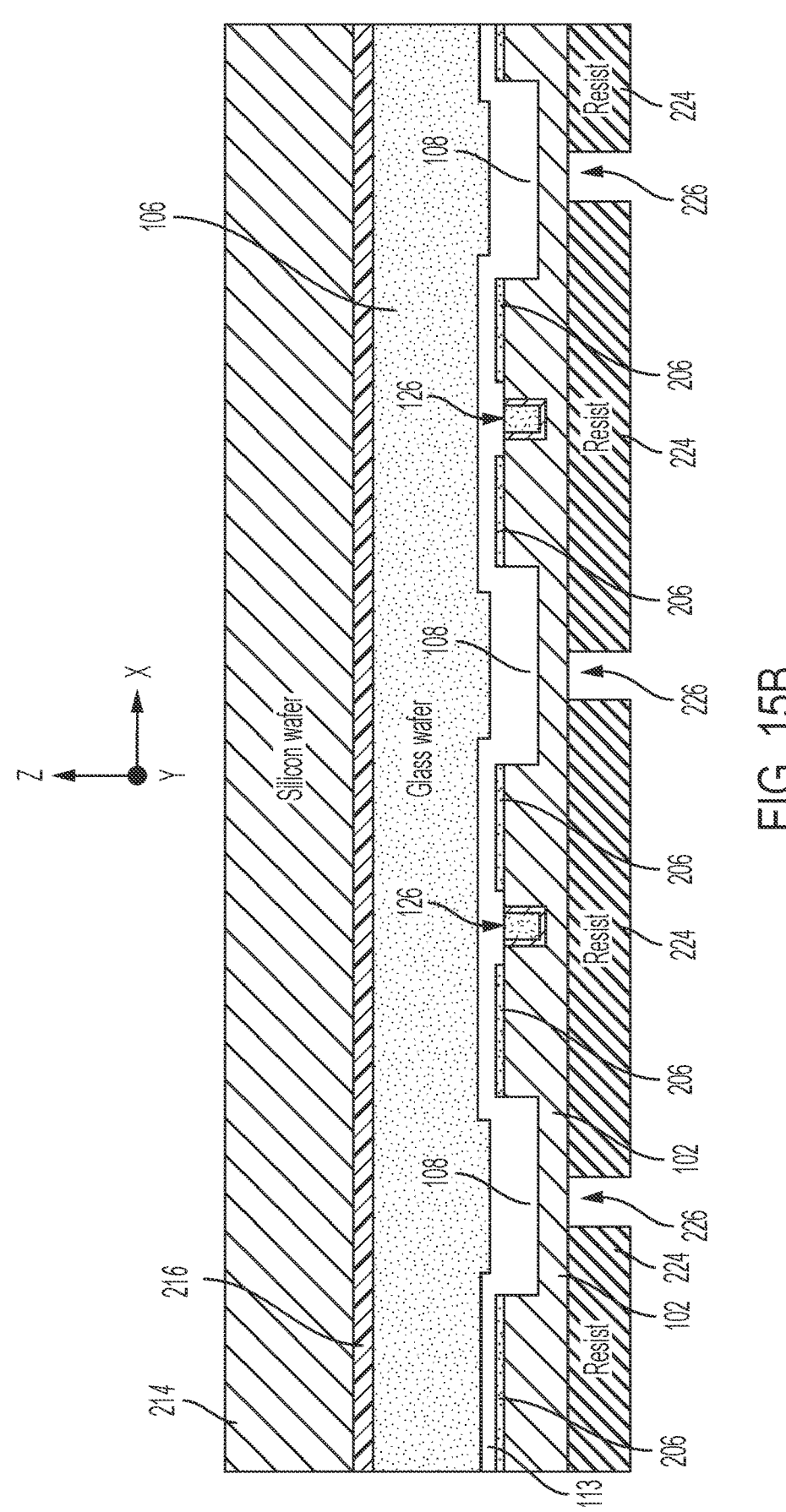
Figure 15C:
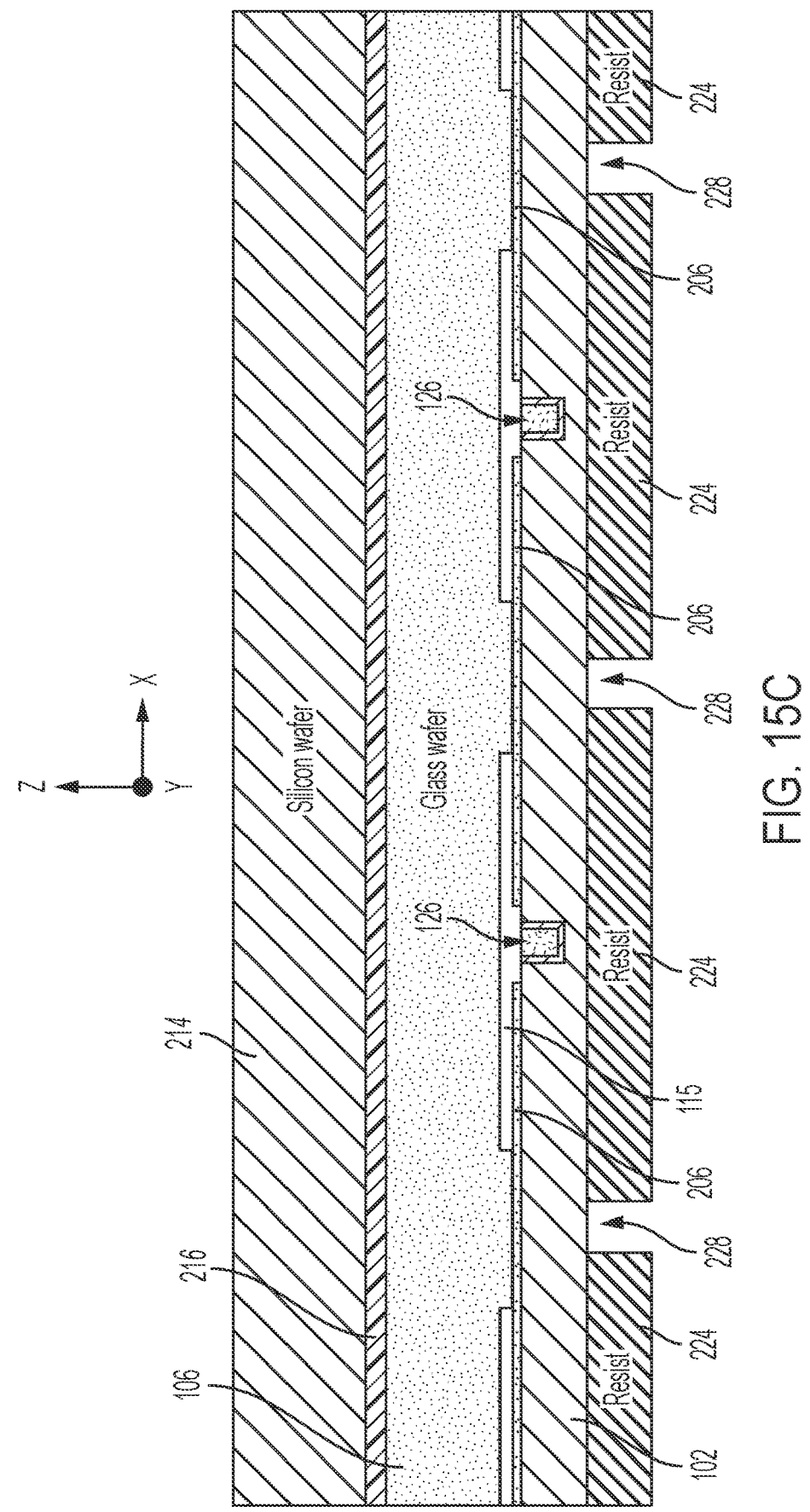
Figure 16A:
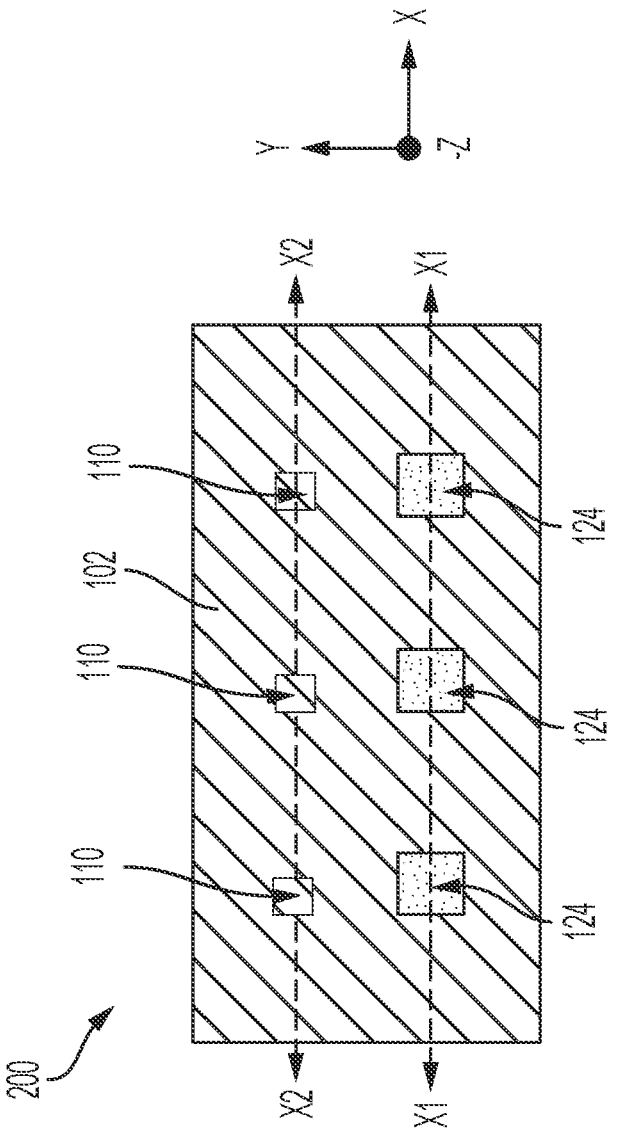
Figure 16B:
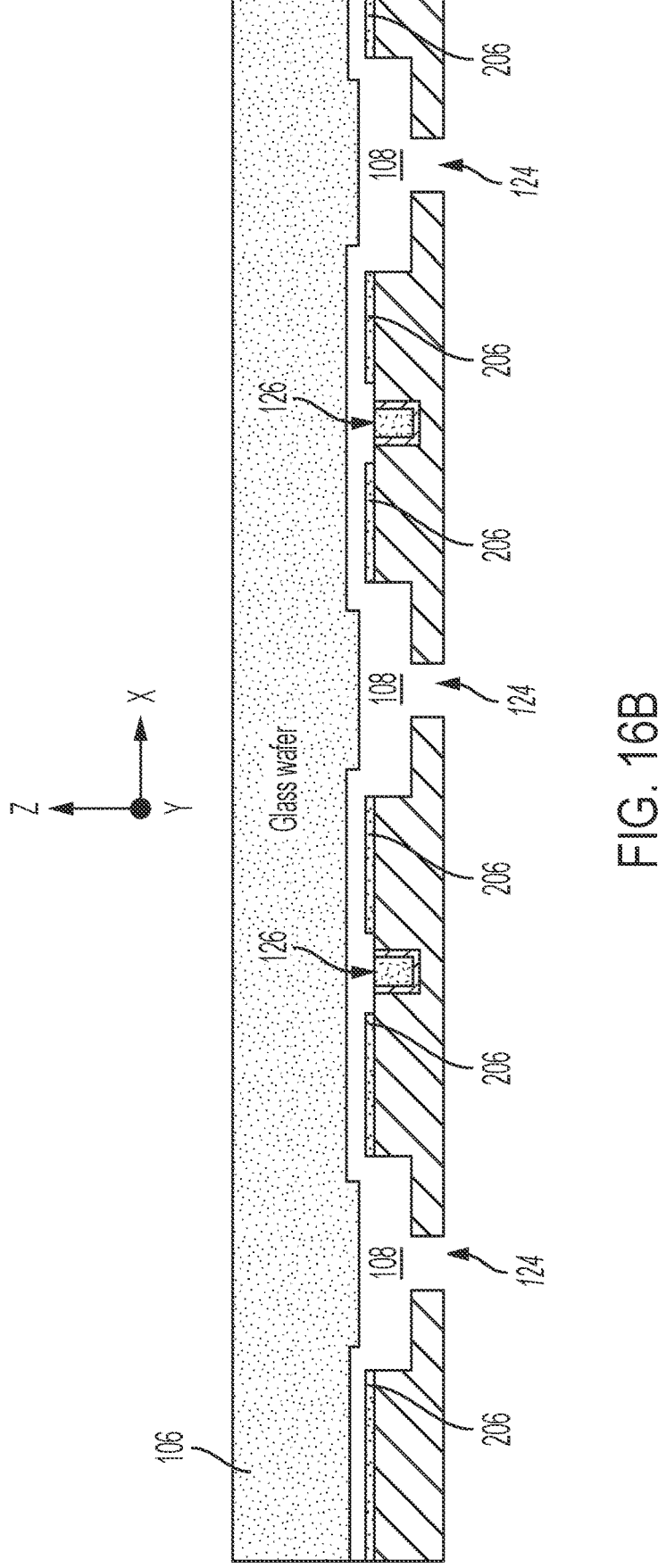
Figure 16C:
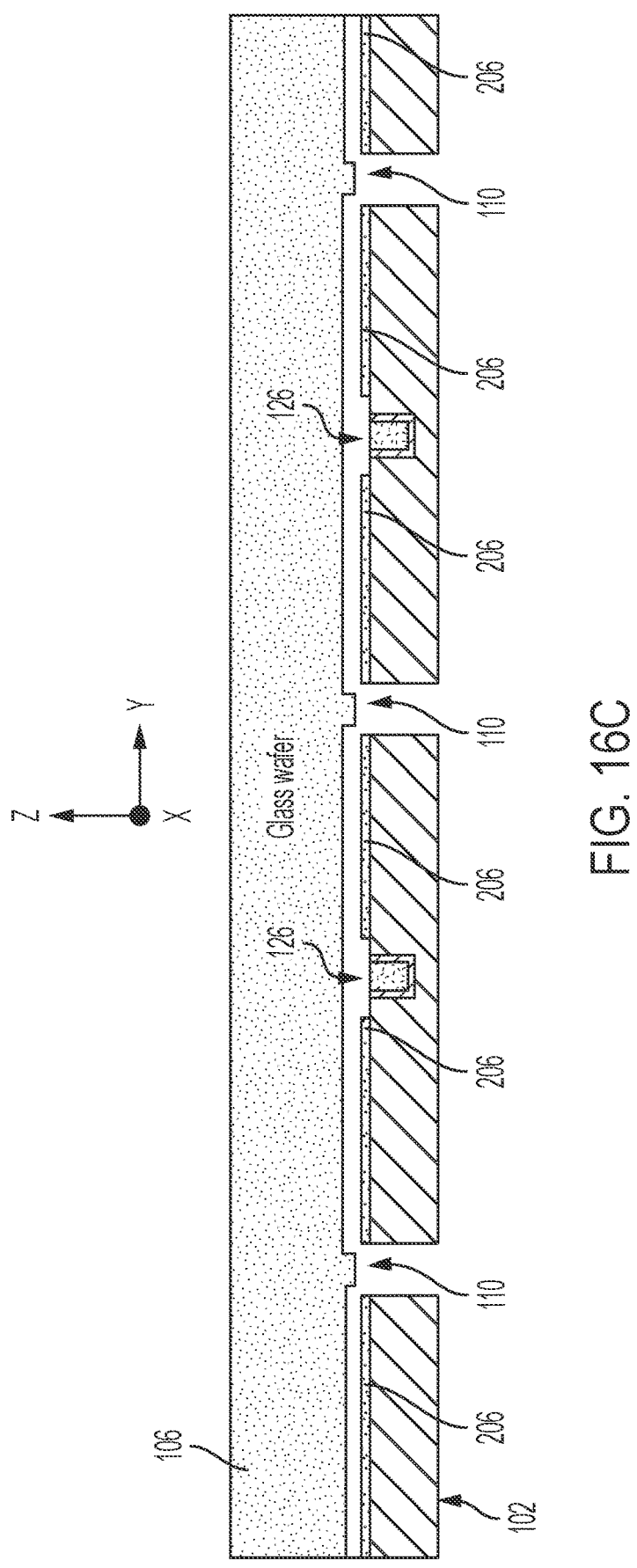
Figure 17A:
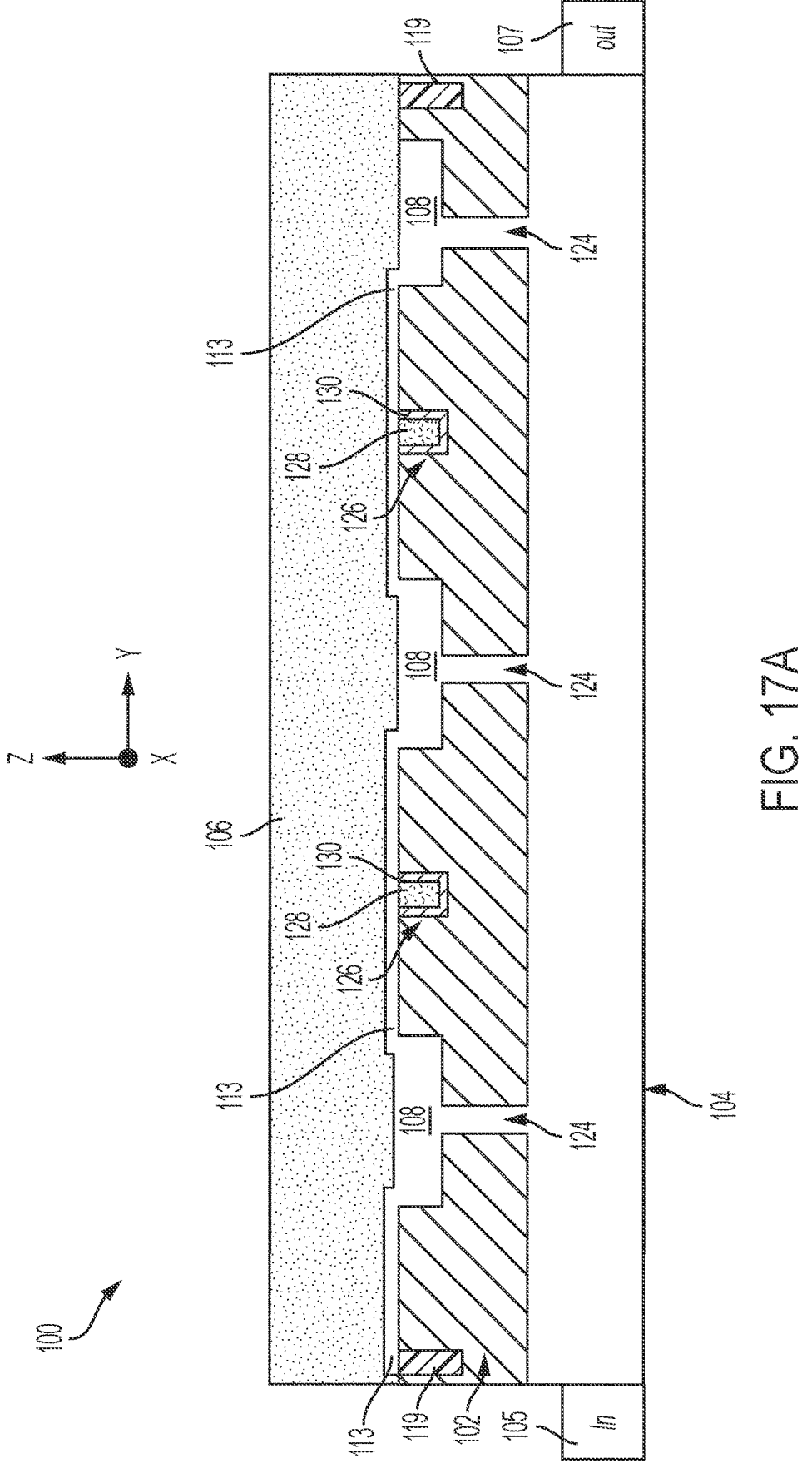
Figure 17B:
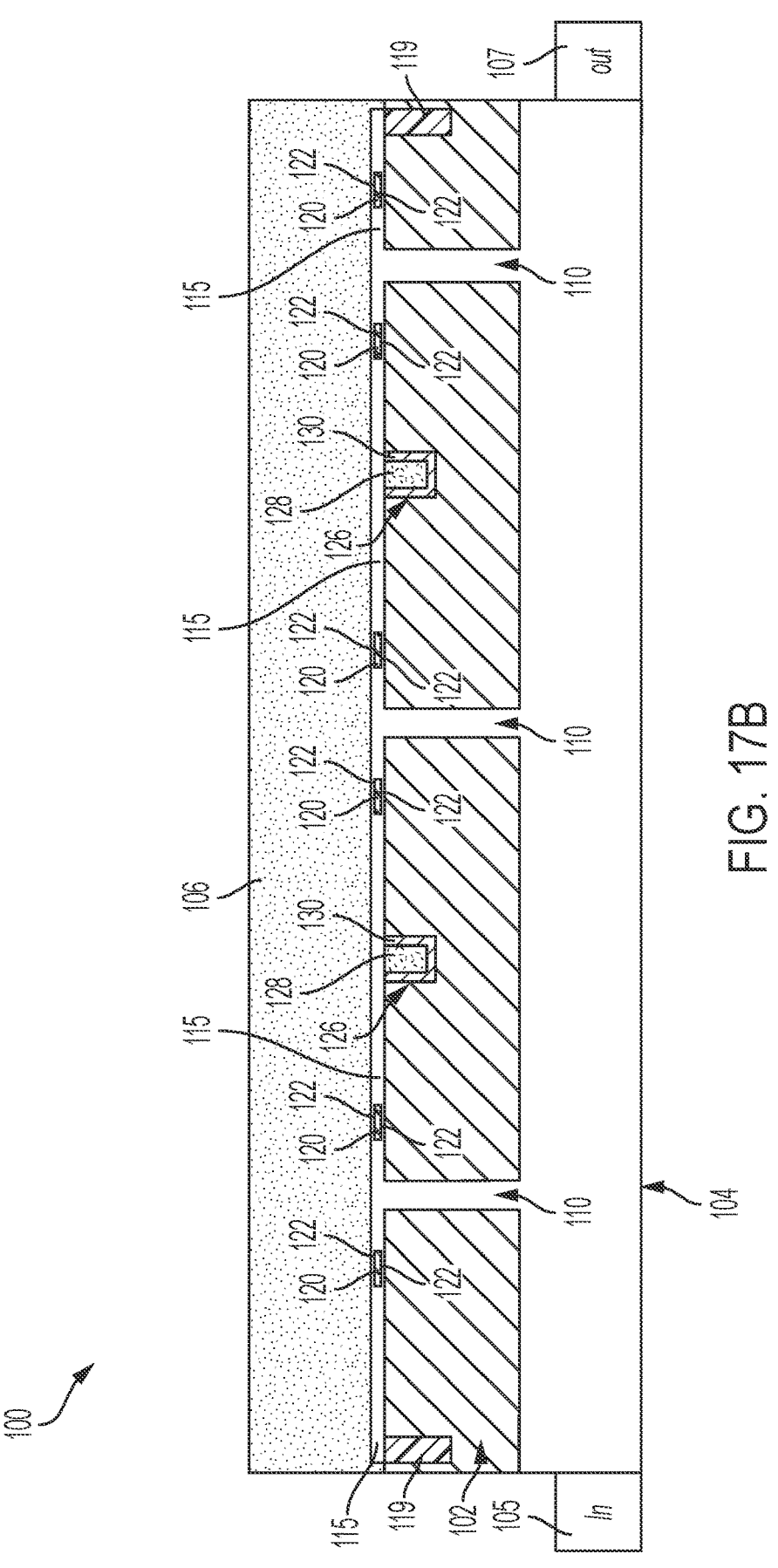
Figure 18A:
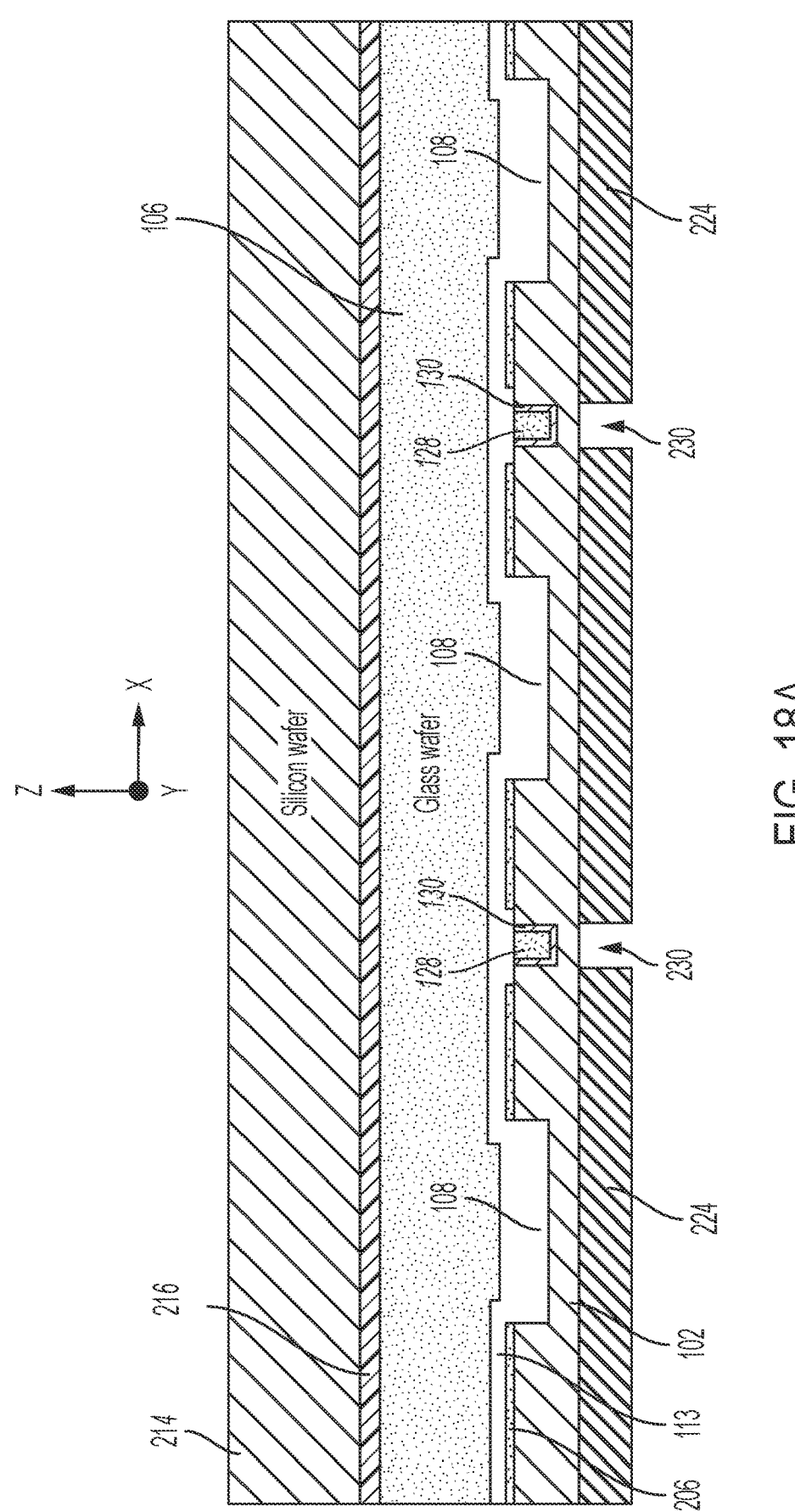
Figure 18B:
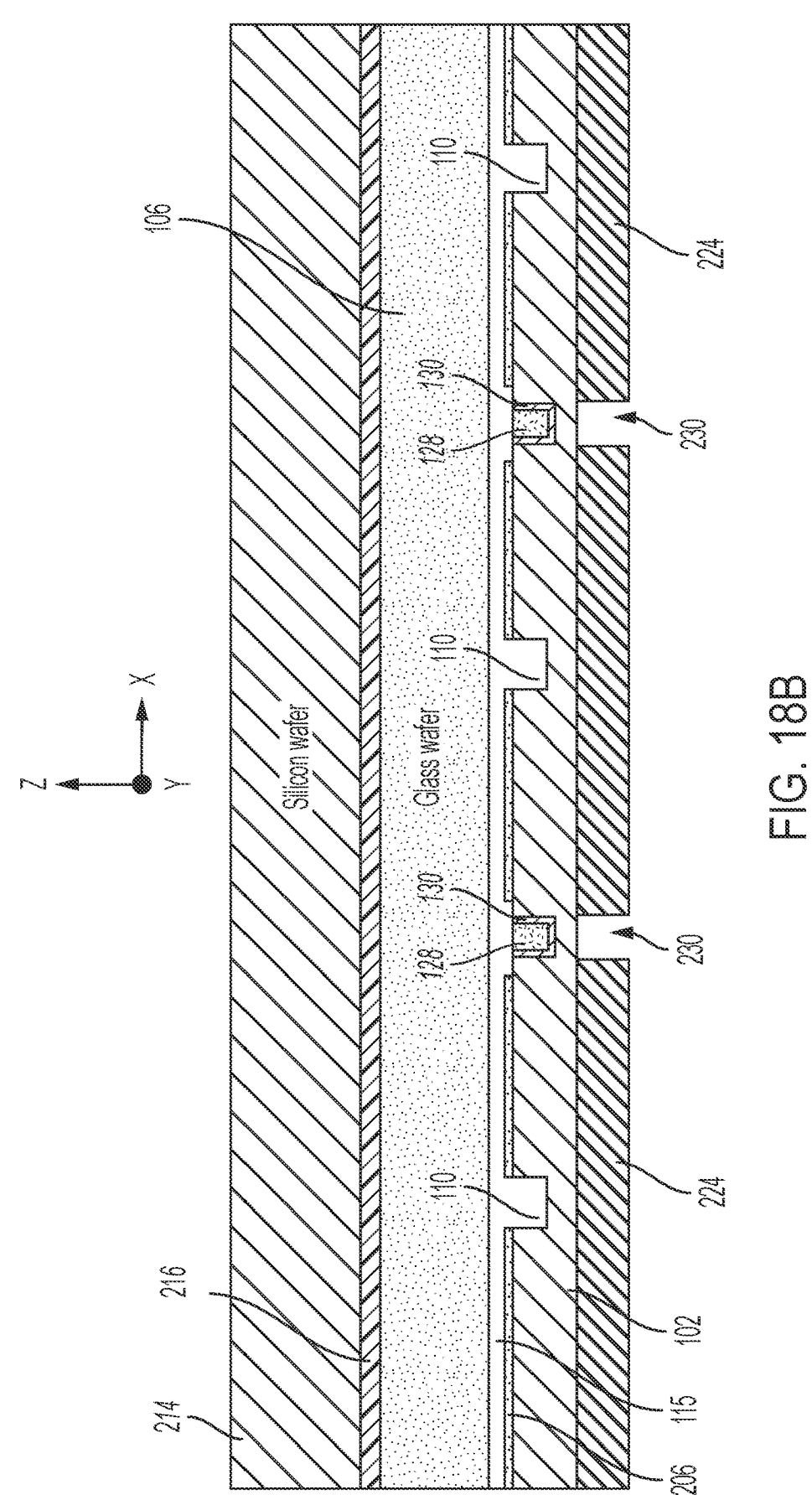
Figure 19A:
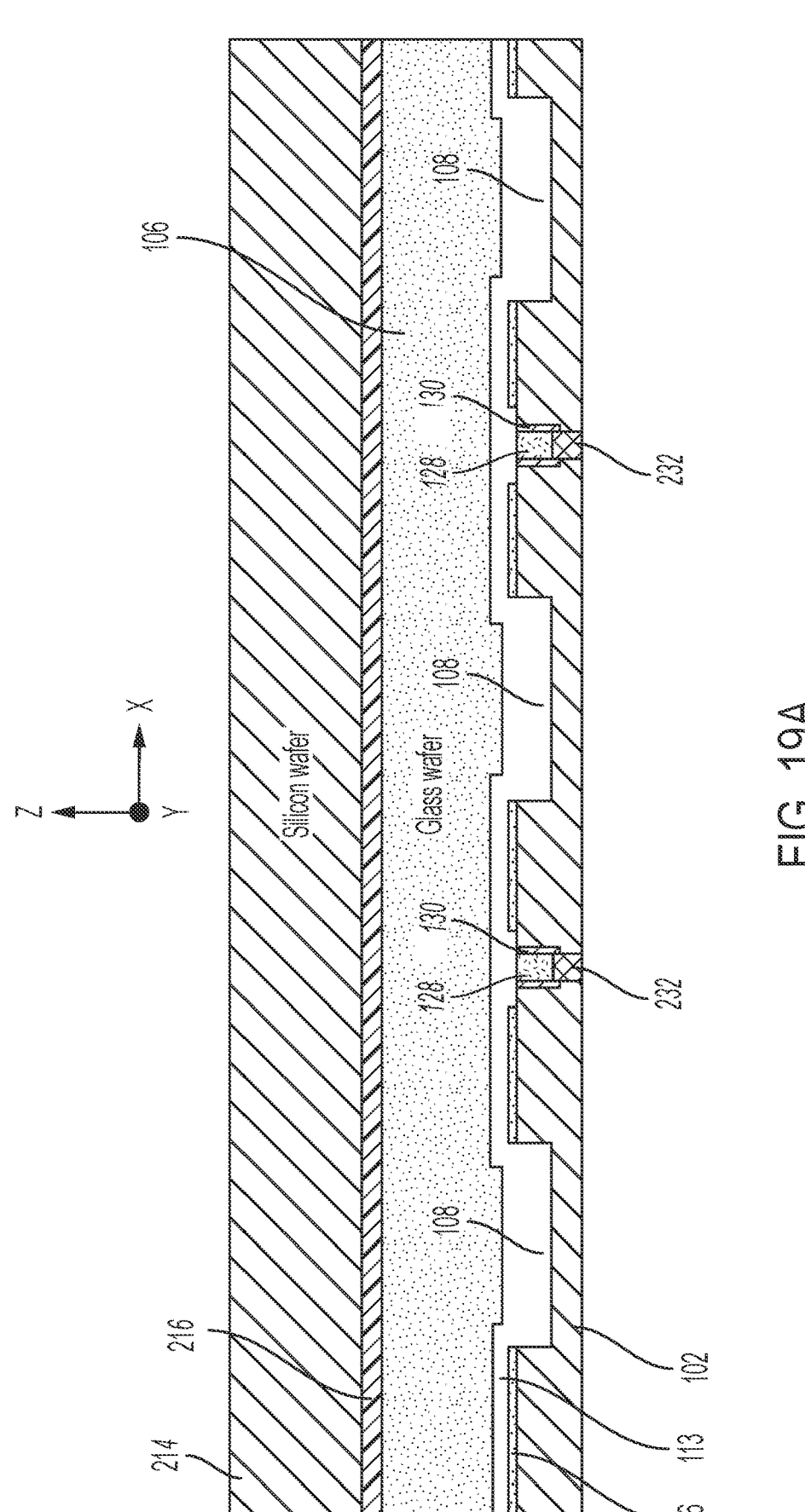
Figure 19B:
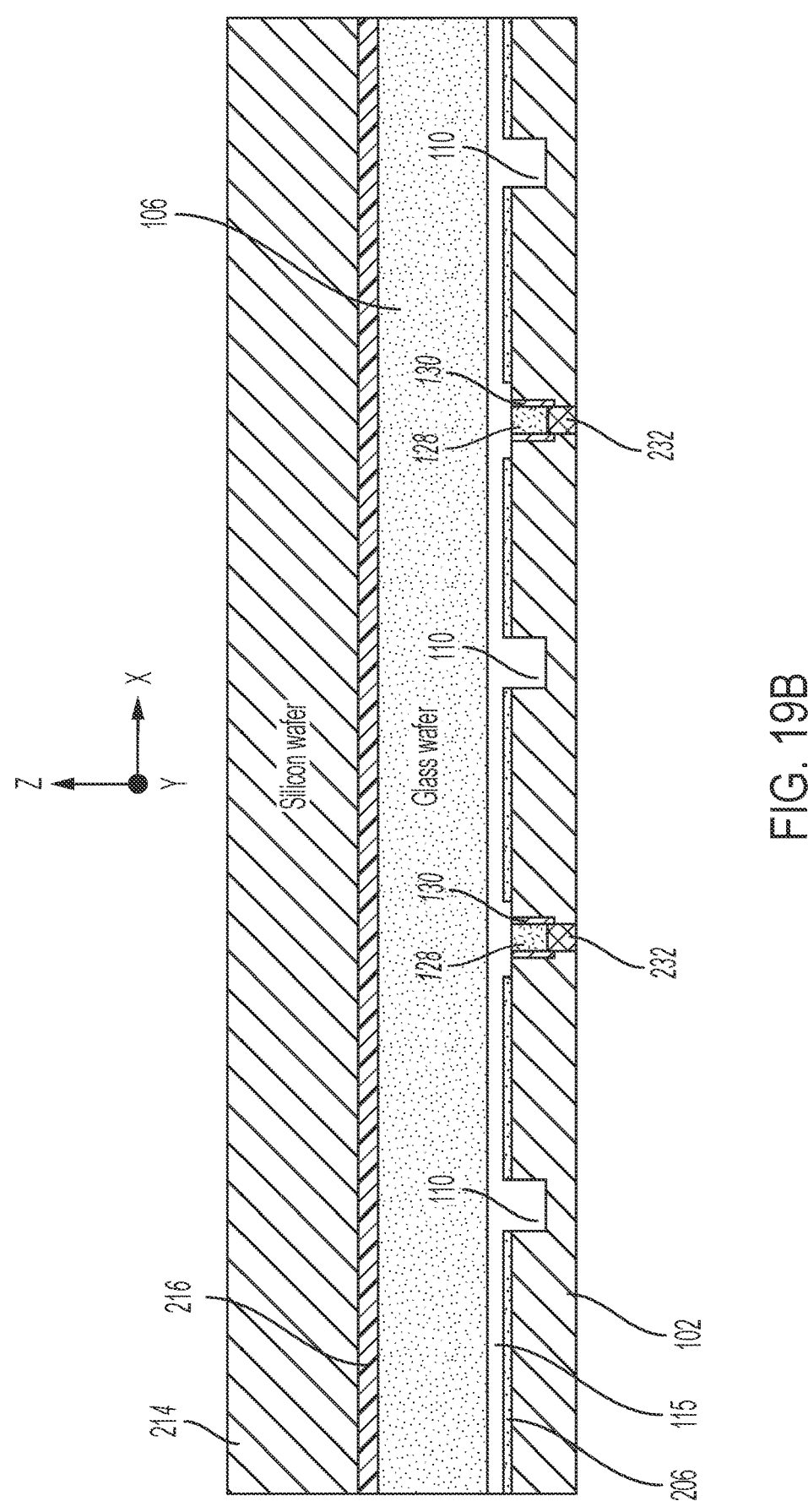

FIGS. 2-19B are a series of views illustrating a method of forming a neural lattice device according to exemplary embodiments of the present teachings, in which:

FIG. 2 is a cross-section view illustrating the neural lattice device in the first orientation following one or more subsequent fabrication processes;

FIG. 3 is a cross-section view illustrating the neural lattice device in the first orientation following one or more subsequent fabrication processes;

FIG. 4 is a cross-section view illustrating the neural lattice device in the first orientation following one or more subsequent fabrication processes;

FIG. 5 is a cross-section view illustrating the neural lattice device in the first orientation following one or more subsequent fabrication processes;

FIG. 6 is a cross-section view illustrating the semiconductor device in the first orientation following one or more subsequent fabrication processes;

FIG. 7 is a cross-section view illustrating the neural lattice device in the first orientation following one or more subsequent fabrication processes;

FIG. 8A is a top view of the neural lattice device following one or more subsequent fabrication processes;

FIG. 8B is a cross-section view illustrating the neural lattice device in the first orientation;

FIG. 9A is a top view of the neural lattice device following one or more subsequent fabrication processes;

FIG. 9B is a cross-section view illustrating the neural lattice device in the first orientation;

FIG. 10A is a top view of the neural lattice device following one or more subsequent fabrication processes;

FIG. 10B is a cross-section view illustrating the neural lattice device in the first orientation;

FIG. 11A is a top view of the neural lattice device following one or more subsequent fabrication processes;

FIG. 11B is a cross-section view illustrating the neural lattice device in the first orientation;

FIG. 12A is a top view of the neural lattice device following one or more subsequent fabrication processes;

FIG. 12B is a cross-section view illustrating the neural lattice device in the first orientation;

FIG. 13A is a top view of the neural lattice device following one or more subsequent fabrication processes;

FIG. 13B is a cross-section view illustrating the neural lattice device in the first orientation;

FIG. 14A is a cross-section view illustrating the neural lattice device in the first orientation following one or more subsequent fabrication processes;

FIG. 14B is a cross-section view illustrating the neural lattice device in the second orientation following one or more subsequent fabrication processes;

FIG. 15A is a bottom view of the neural lattice device following one or more subsequent fabrication processes;

FIG. 15B is a cross-section view illustrating the neural lattice device in the first orientation;

FIG. 15C is a cross-section view illustrating the neural lattice device in the second orientation;

FIG. 16A is a bottom view of the neural lattice device following one or more subsequent fabrication processes;

FIG. 16B is a cross-section view illustrating the neural lattice device in the first orientation;

FIG. 16C is a cross-section view illustrating the neural lattice device in the second orientation;

FIG. 17A is a cross-section view illustrating the neural lattice device in the first orientation following one or more subsequent fabrication processes;

FIG. 17B is a cross-section view illustrating the neural lattice device in the second orientation following one or more subsequent fabrication processes;

FIG. 18A is a cross-section view illustrating the neural lattice device in the first orientation following one or more subsequent fabrication processes;

FIG. 18B is a cross-section view illustrating the neural lattice device in the second orientation following one or more subsequent fabrication processes;

FIG. 19A is a cross-section view illustrating the neural lattice device in the first orientation following one or more subsequent fabrication processes; and FIG. 19B is a cross-section view illustrating the neural lattice device in the second orientation following one or more subsequent fabrication processes.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the present invention are described herein with reference to the related drawings. Alternative embodiments can be devised without departing from the scope of this invention. It is noted that various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements. It should be noted, the term "selective to," such as, for example, "a first element selective to a second element," means that a first element can be etched and the second element can act as an etch stop.

For the sake of brevity, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details. For example, a description of a substrate and/or a semiconductor device to form various features (e.g., cavities, openings, trenches, holes, etc.) following various lithography and patterning operations can include various well-known deposition, lithography, photoresist, and etchings processes and techniques.

Turning now one or more non-limiting embodiments of the invention, a neural lattice device and fabrication methods thereof are provided. The neural lattice device is configured to perform characterization of neuron behavior. The neural lattice device is a patterned, microfluidic template configured to hold biological neurons and to provide chemical, electrical and/or magnetic stimulation capable of facilitating neuron cultivation and growth.

With reference now to the drawings, FIGS. 1A, 1B and 1C illustrate a neural lattice device 100 is illustrated according to a non-limiting embodiment. The neural lattice device 100 includes a semiconductor substrate 102, a reservoir 104, and a cover 106. The semiconductor substrate 102 extends along a first axis (e.g. X-axis) to define length, a second axis (e.g., Y-axis) orthogonal to the X-axis to define a width, and a third axis (e.g., Z-axis) to define a height. The semiconductor substrate can be formed from various semiconductor materials including, but not limited to, silicon (Si).

The semiconductor substrate 102 includes one or more wells 108, one or more supply ducts 110, and a channel network 112. The cover 106 is disposed against an upper surface of the semiconductor substrate 102 and is configured to hermetically seal the wells 108, the supply ducts 110, and the channel network 112. Each wells 108 is configured to contain a biological neuron (not shown) therein. The biological neuron can include, for example, a stem cell. The supply ducts 110 are configured to receive a nutrient fluid and continuously deliver the nutrient fluid. The nutrient fluid feeds the biological neurons contained in a given well 108. The continuous delivery of nutrient fluid to causes the biological neurons to develop and grown axons, which extend through channel network.

The channel network 112 includes one or more channels. The channels define an internal area that allows fluid to flow therethrough. Accordingly, the channel included in the channel network 112 establish fluid communication among the wells 108 and the supply ducts 110. According to one or more non-limiting embodiments, channels includes one or more growth channels 113, one or more supply channels 115, one or more bridge channels 117, and one or more drain channels 119. The growth channels 113 establish fluid communication between a first well 108 and a second well 108. The supply channels 115 establish fluid communication between a first supply duct 110 and a well 108, or between a first supply duct 110 and a second supply duct 110. The bridge channels 117 establish fluid communication between a first growth channel 113 and a second growth channel 113. The drain channels 119 are in fluid communication with the growth channels 113 and the supply channels 115, and are configured to provide a drain path to deliver waste from the wells 108 and/or the supply ducts to a waste receptacle (not shown).

The neural lattice device 100 further includes at least one growth barrier 120 and one or more one wiring structures 126. Each growth barrier 120 is disposed in a given channel included in the channel network 112 and has a size less than the internal area of a respective channel to define spacings between a given barrier 120 and sidewalls of the channel. In one or more non-limiting embodiments, the spacings are defined by a distance between the barrier 120 and the channel of about 500 nanometers (nm), for example. In this manner, the growth barriers 120 partially block a given channel while still allowing fluid to flow therethrough. The growth barrier 120 further allow the axons to grow and extend through the growth channels 113 to facilitate connection between axons of different individual neurons grown from respective wells 108, while blocking the axons from extending into the supply ducts 110.

The growth barriers 120 can be formed as one or more pillars, which are etched using various known lithography processes, and can be formed when forming the growth channels 113. According to one or more non-limiting embodiments, a plurality of growth barriers 120 are disposed in the channels to surround a given supply duct 110. For example, a first growth barrier 120 can be disposed in a first supply channel 115 extending from a first supply duct 110 to a first well 108. A second growth barrier 120 can be disposed in a second supply channel 115 extending from the first supply duct 110 to a second well 108. A third growth barrier 120 can be disposed in a third supply channel 115 extending from the first supply duct 110 to a second supply duct 110. A fourth growth barrier 120 can disposed in a fourth supply channel 115 which extends from the second supply duct 110 to a third supply duct 110, or which extends from the first supply duct 110 to the at last one drain channel 119.

The wiring structure 126 is embedded in the semiconductor substrate 102 to establish electrical connection with a power source (not shown). The wiring structures 126 can facilitate stimulation and sensing of the biological neurons contained in a given well 108, which can aid or inhibit cell growth, depending on the stimulation paradigm. The wiring structures 126 can be placed in signal communication with one or more of wells via one or more electrically conductive traces (not shown) and can perform one or both of deliver electrical current to the well 108 and/or receive electrical potential from the well 108. For example, electrical current output from the wiring structure 126 can be delivered to stem cells loaded in a well 108 via the electrically conductive traces. In one or more non-limiting embodiments, stimulation can take two forms. In a first form, simulation can involve the electrical stimulation of a neuron to induce a change in the state of its neural activation. In another sense, the electrical stimulation can serve to induce a stem cell to grow, form axons and dendrites, and also form synapse structures. Meanwhile, the sensing capabilities can allow monitoring of the neuronal health and can be used to measure the interaction of neurons in network. The sensing capability can sense growth or development of stem cell growth based on the electrical potential of corresponding neurons. For example, a sensor (not shown) can be connected to one or more of the wiring structures 126 to detect electrical potential changes occurring in a given well 108. Accordingly, the sensors can detect neural spiking (e.g. growth) of neurons in response to sensing the electrical potential change or a "spike" in the sensed electrical potential.

The wiring structure 126 includes an electrically conductive element 128 and a dielectric layer 130 surrounding the electrically conductive element 128. The dielectric layer 130 can include various dielectric materials such as silicon oxide ($SiO_2$) or silicon nitride (SiN), and is formed against the semiconductor substrate 102. The electrically conductive element 128 can be formed from various electrically conductive materials, and is formed directly against the dielectric layer 130. The electrically conductive material of the conductive element 128 can include, but is not limited to, glassy carbon, or titanium (Ti), and platinum (Pt). Accordingly, the dielectric layer 130 surrounds the sidewalls and base of the electrically conductive element 128, while exposing an upper surface of the electrically conductive element 128.

The reservoir 104 is coupled to a bottom surface of the semiconductor substrate 102. The reservoir 104 includes an inlet 105 configured to deliver a fluid into the reservoir 104 and an outlet 107 configured to discharge the fluid from the reservoir 104. One or more well-vias 124 and formed in the semiconductor substrate 102. Each well-via 124 establishes fluid communication with the reservoir 104 and a respective well 104. The supply duct 110 is configured to establish fluid communication with the reservoir 104 and a supply source (not shown).

FIGS. 2 through 19B are a series of views illustrating a method of forming a neural lattice device according to non-limiting exemplary embodiments of the invention. Turning to FIG. 2, a starting semiconductor substrate 102 is illustrating after patterning a resist layer 200. The patterned resist layer 200 includes one or more resist openings 202 corresponding to a location at which to form a wiring structure 126 in the substrate 102.

Turning to FIG. 3, the semiconductor substrate 102 is illustrated after transferring the resist openings 202 into the semiconductor substrate 102 to form corresponding wiring structure trenches 204. In one or more non-limiting embodiments, a reactive ion etch (RIE) process can be performed to transfer the resist openings 202 into the semiconductor substrate 102. The resist layer 202 can then be removed after forming the wiring structure trenches 204.

Referring to FIG. 4, the semiconductor substrate 102 is illustrated after depositing a dielectric layer 130 on an upper surface of the semiconductor substrate 102. The dielectric layer 130 can include various dielectric materials such as, for example, $SiO_2$ or SiN, and can have thickness ranging, for example, from about 5 nm to about 20 nm. In some non-limiting embodiments of the invention, the dielectric layer 130 can have thickness ranging from about 250 nm to 2000 nm when aiming to form thick provide thick insulation layers if desired. According to one or more non-limiting embodiments, a conformal deposition process is performed such that the dielectric layer 130 conforms to the sidewalls and bottom of the wiring structure trenches 204. The conformal deposition process can include, for example, an atomic layer deposition (ALD) process or a chemical vapor deposition (CVD) process.

At FIG. 5, the semiconductor substrate 102 is illustrated after depositing an electrically conductive material 128 on an upper surface of the dielectric layer 130. The electrically conductive material can include various metal materials such as, for example, glassy carbon, platinum (Pt), and titanium (Ti). In one or more non-limiting embodiments, an ALD process is performed to overfill the wiring structure trenches 204. Accordingly, the dielectric layer 130 is interposed between the conductive material 128 and the semiconductor substrate 102.

Turning to FIG. 6, the semiconductor substrate 102 is illustrated after removing a portion of the electrically conductive material 128 and dielectric material 130 from the substrate upper surface. In one or more non-limiting embodiments, a chemical-mechanical planarization (CMP) process is performed, which stops on the upper surface of the semiconductor substrate 102. The remaining portions of the dielectric material 130 and conductive material 128 filling the wiring trenches form the dielectric layer 130 and the electrically conductive of a one wiring structure 126 in the substrate 102.

At FIG. 7, the semiconductor substrate 102 is illustrated following deposition of a dielectric layer 206. According to one or more non-limiting embodiments, the dielectric layer 206 can be formed by performing a deposition process such as ALD, for example, which deposits the dielectric layer 206 on the upper surface of the semiconductor substrate 102 and covers the wiring structures 126. The dielectric layer 206 can include various dielectric materials including, but not limited to, $SiO_2$ and SiN, and can have a thickness ranging, for example, from about 5 nm to about 30 nm.

Referring now to FIGS. 8A and 8B, the semiconductor substrate 102 is illustrate after patterning the dielectric layer 206 to form openings 208 that expose a respective underlying wiring structure 126 and a portion of the upper surface of the substrate 102.

Turning to FIGS. 9A and 9B, the semiconductor substrate 102 is illustrated after patterning a resist layer 210 formed on an upper surface of the dielectric layer 206. The resist layer 210 can be patterned to form one or more well openings 212. The well openings 212 expose a portion of the underlying dielectric layer 206, and are formed at locations designated to contain corresponding wells 108 as described herein.

Referring to FIGS. 10A and 10B, the semiconductor substrate 102 is illustrated after transferring the well openings 212 into the semiconductor substrate 102 to form corresponding wells 108. In one or more non-limiting embodiments, a reactive ion etch (RIE) process can be performed to transfer the well openings 212 into the semiconductor substrate 102. In one or more non-limiting embodiments, the wells 108 can be formed with a depth $_{WELL}$ (extending along the Z-axis) ranging, for example, from about 25 micrometers (μm) to about 100 μm With reference now to FIGS. 11A, 11B, 12A, 12B, 13A, 13B, 14A and 14B, a series of drawings illustrates a process flow for fabricating a hermetically sealing cover 106 according to non-limiting embodiments of the invention. At FIGS. 11A and 11B, a cover layer 106 is formed on an upper surface of a handle wafer 214. In one or more non-limiting embodiments, the cover layer 106 can include a glass material, and can be fixed (e.g., bonded) to the handle wafer 214 using a layer of releasable bonding adhesive 216. In one or more non-limiting embodiments, the cover layer 106 has a thickness (e.g., extending along the Z-axis) ranging from about 100 μm to about 300 μm.

Turning to FIGS. 12A and 12B, the cover layer 106 is illustrated following patterning of a resist layer 218 formed the cover layer upper surface. The resist layer 218 is patterned to form one or more opening 220 that expose portions of the cover layer 106. As shown in FIGS. 13A and 13B, the resist openings 220 can be transferred into the cover layer 106 using a RIE process, for example, to form corresponding cover trenches 222. In one or more non-limiting embodiments of the invention, the trenches 222 are utilized to grow the axons and dendrites of a neurons deposited in the wells 108. In one or more non-limiting embodiments, the cover trenches 222 can be formed with a depth ranging, for example, from about 2 μm to about 10 μm, which allow axons and dendrites to grow while inhibiting growth of the cell bodies.

Turning to FIGS. 14A and 14B, the patterned cover layer 106 is illustrated after being flipped and disposed on an upper surface of the semiconductor substrate 102. According to one or more non-limiting embodiments of the invention, the patterned cover layer 106 can be anodically bonded to the semiconductor substrate to provide a cover 106 that hermetically seals the wells 108, the supply ducts 110 and the channel network 112, e.g., the growth channels 113 and the supply channels 115.

With reference to FIGS. 15A, 15B, 16A, 16B, 17A and 17B, a series of drawings illustrates a process flow for assembling a reservoir 104 to the semiconductor substrate of a neural lattice device 100 according to non-limiting embodiments of the invention. At FIGS. 15A, 15B and 15C, the semiconductor substrate 102 is illustrated after patterning a resist layer 224 that is formed on the substrate bottom surface. The patterned resist layer 224 can include one or more well-via openings 226 (see FIG. 15B) and one or more duct openings 228 (see FIG. 15C). The well-via openings 226 are formed at locations below a respective well 108. The duct openings 228 are formed at locations designated for forming a supply duct 110 in the substrate 102.

Turning to FIGS. 16A, 16B and 16C, the semiconductor substrate 102 is illustrated after transferring the well-via openings 226 and the duct openings 228 into the semiconductor substrate 102, and removing the handle wafer 216 and bonding layer 214. A CMP process can be performed until reaching the cover 106 to remove the handle wafer 216 and bonding layer 214. A RIE process can be performed to transfer the well-via openings 226 and the duct openings 228 into the semiconductor substrate 102 to form corresponding well-vias 124 and supply ducts 110. The well-vias 124 establish a fluid path into a respective well 108 and to the growth paths 113, while the ducts 110 establish a fluid path to the supply paths 115. The patterned resist layer 224 can then be removed after forming the well-vias 124 and the ducts 110.

At FIGS. 17A and 17B, a reservoir 104 is shown coupled to the bottom surface of the substrate 102. In one or more non-limiting embodiments of the invention, an anodic bonding process can be performed to attach the reservoir 104 to the substrate 102. In some non-limiting embodiments of the invention, a dual-sided adhesive rubber O-ring can be used to attach and seal the reservoir 104 to the substrate 102.

The reservoir 104 includes an inlet 105, an outlet 107, one or more openings in fluid communication with a corresponding well-via 124, and one or more openings in fluid communication with a corresponding supply duct 110. The inlet is 105 configured to deliver a fluid into the reservoir 104 and an outlet 107 is configured to discharge the fluid from the reservoir 104. According to a non-limiting embodiment of the invention, the nutrient medium and/or stem cell placement solution can include a culturing medium, horse serum, sodium pyruvate, GlutaMAX, and insulin, and various combinations thereof.

As described herein, a constant nutrient supply is maintained between the inlet 105 and outlet 107. Nutrients and neurons are forced into the channels due to pressure differential between the reservoir 104 and the channels 113, 115 and 117 using principles of microfluidics. Accordingly, a controlled flow of materials can be effected in the supply ducts 110 and the wells 108 and the flow rates can be modulated by altering the original flow rate. In addition, the control flow also enable auto-placement of stem cells in the well 108.

Referring now to FIGS. 18A, 18B, 19A and 19B, a series of drawings illustrates a process flow to form wire contact pads capable of providing electrical connection for a neural lattice device 100 according to non-limiting embodiments of the present invention. At FIGS. 18A and 18B, the semiconductor substrate 102 is illustrated after patterning a resist layer 224 that is formed on the substrate bottom surface. The patterned resist layer 224 includes one or more wiring openings 230. The wiring openings 230 are formed at locations below a respective wiring structures 126. As described herein, the wiring structures 126 include an electrically conductive element 128 and a dielectric layer 130 surrounding the electrically conductive element 128.

Turning to FIGS. 19A and 19B, the semiconductor substrate 102 is illustrated after transferring the wiring openings 128 defined by the resist layer 224 into the substrate 102 to expose the underlying electrically conductive element 128. In one or more non-limiting embodiments of the invention, transferring the wiring openings 128 into the substrate 102 includes performing an etching process that removes a portion of the dielectric layer 130 and directly exposes a surface of the electrically conductive element 128. Thereafter, the resist layer 224 is removed from the substrate 102 and an electrically conductive material 232 is deposited in the wiring openings 128 to contact the exposed surface of the electrically conductive element 128. In one or more non-limiting embodiments of the invention, the electrically conductive material 232 overfills the wiring openings 128 and an excess portion of conductive material 232 is formed on the surface of the substrate 102. A CMP process is then performed to remove excess portion of conductive material 232 from the surface of the substrate 102 such that wiring contacts 232 are formed, which are flush (co-planar) with the substrate surface and establish electrical conductivity with the electrically conductive element 128.

As described herein, one or more non-limiting embodiments of the invention provide a neural lattice device and fabrication methods thereof are provided. The neural lattice device is configured to perform characterization of neuron behavior. The neural lattice device is a patterned, microfluidic template configured to hold biological neurons and to provide chemical, electrical and/or magnetic stimulation capable of facilitating neuron cultivation and growth.

Various embodiments of the present invention are described herein with reference to the related drawings. Alternative embodiments can be devised without departing from the scope of this invention. Although various connections and positional relationships (e.g., over, below, adjacent, etc.) are set forth between elements in the following description and in the drawings, persons skilled in the art will recognize that many of the positional relationships described herein are orientation-independent when the described functionality is maintained even though the orientation is changed. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The phrase "selective to," such as, for example, "a first element selective to a second element," means that the first element can be etched and the second element can act as an etch stop.

As previously noted herein, for the sake of brevity, conventional techniques related to semiconductor device and integrated circuit (IC) fabrication may or may not be described in detail herein. By way of background, however, a more general description of the semiconductor device fabrication processes that can be utilized in implementing one or more embodiments of the present invention will now be provided. Although specific fabrication operations used in implementing one or more embodiments of the present invention can be individually known, the described combination of operations and/or resulting structures of the present invention are unique. Thus, the unique combination of the operations described in connection with the fabrication of a semiconductor device according to the present invention utilize a variety of individually known physical and chemical processes performed on a semiconductor (e.g., silicon) substrate, some of which are described in the immediately following paragraphs.

In general, the various processes used to form a microchip that will be packaged into an IC fall into four general categories, namely, film deposition, removal/etching, semiconductor doping and patterning/lithography. Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others. Removal/etching is any process that removes material from the wafer. Examples include etch processes (either wet or dry), and chemical-mechanical planarization (CMP), and the like. Semiconductor doping is the modification of electrical properties by doping, for example, transistor sources and drains, generally by diffusion and/or by ion implantation. These doping processes are followed by furnace annealing or by rapid thermal annealing (RTA). Annealing serves to activate the implanted dopants. Films of both conductors (e.g., poly-silicon, aluminum, copper, etc.) and insulators (e.g., various forms of silicon dioxide, silicon nitride, etc.) are used to connect and isolate transistors and their components. Selective doping of various regions of the semiconductor substrate allows the conductivity of the substrate to be changed with the application of voltage. By creating structures of these various components, millions of transistors can be built and wired together to form the complex circuitry of a modern microelectronic device.

As noted above, atomic layer etching processes can be used in the present invention for via residue removal, such as can be caused by via misalignment. The atomic layer etch process provide precise etching of metals using a plasma-based approach or an electrochemical approach. The atomic layer etching processes are generally defined by two well-defined, sequential, self-limiting reaction steps that can be independently controlled. The process generally includes passivation followed selective removal of the passivation layer and can be used to remove thin metal layers on the order of nanometers. An exemplary plasma-based approach generally includes a two-step process that generally includes exposing a metal such a copper to chlorine and hydrogen plasmas at low temperature (below 20-C). This process generates a volatile etch product that minimizes surface contamination. In another example, cyclic exposure to an oxidant and hexafluoroacetylacetone (Hhfac) at an elevated temperature such as at 275° C. can be used to selectively etch a metal such as copper. An exemplary electrochemical approach also can include two steps. A first step includes surface-limited sulfidization of the metal such as copper to form a metal sulfide, e.g., $Cu_2S$, followed by selective wet etching of the metal sulfide, e.g., etching of $Cu_2S$ in HCl. Atomic layer etching is relatively recent technology and optimization for a specific metal is well within the skill of those in the art. The reactions at the surface provide high selectivity and minimal or no attack of exposed dielectric surfaces.

Semiconductor lithography is the formation of three-dimensional relief images or patterns on the semiconductor substrate for subsequent transfer of the pattern to the substrate. In semiconductor lithography, the patterns are formed by a light sensitive polymer called a photoresist. To build the complex structures that make up a transistor and the many wires that connect the millions of transistors of a circuit, lithography and etch pattern transfer steps are repeated multiple times. Each pattern being printed on the wafer is aligned to the previously formed patterns and slowly the conductors, insulators and selectively doped regions are built up to form the final device.

The photoresist can be formed using conventional deposition techniques such chemical vapor deposition, plasma vapor deposition, sputtering, dip coating, spin-on coating, brushing, spraying and other like deposition techniques can be employed. Following formation of the photoresist, the photoresist is exposed to a desired pattern of radiation such as X-ray radiation, extreme ultraviolet (EUV) radiation, electron beam radiation or the like. Next, the exposed photoresist is developed utilizing a conventional resist development process.

After the development step, the etching step can be performed to transfer the pattern from the patterned photoresist into the interlayer dielectric. The etching step used in forming the at least one opening can include a dry etching process (including, for example, reactive ion etching, ion beam etching, plasma etching or laser ablation), a wet chemical etching process or any combination thereof.

For the sake of brevity, conventional techniques related to making and using aspects of the invention may or may not be described in detail herein. Accordingly, in the interest of brevity, many conventional implementation details are only mentioned briefly herein or are omitted entirely without providing the well-known system and/or process details. For example, a description of patterning a substrate to form various features (e.g., cavities, openings, trenches, holes, etc.) can include the deposition, lithography, photoresist, and etchings processes and techniques described above. Therefore, reference to a patterned substrate and/or patterned semiconductor device at one or more stages of the process flow may omit full details of the deposition, lithography, photoresist, and/or etchings processes and techniques described above for the sake of brevity.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e., one, two, three, four, etc. The terms "a plurality" are understood to include any integer number greater than or equal to two, i.e., two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method of fabricating a neural lattice device, the method comprising:
   forming at least one well in a substrate, the well configured to hold a biological neuron;
   forming at least one supply duct in the substrate, the supply duct configured to receive a nutrient fluid,
   forming in the substrate a channel network including one or more channels configured to establish fluid communication among the at least one well and the at least one supply duct;
   coupling a reservoir to the substrate, the reservoir configured to hold a fluid; and
   disposing a cover against an upper surface of the substrate and configured to hermetically seal the at least one well, the at least one supply duct, and the channel network,
   wherein forming the at least one growth barrier includes forming a plurality of growth barriers surrounding the at least one supply duct.

2. The method of claim 1, further comprising forming one or more well-vias in the substrate, the well-vias configured to establish fluid communication with the reservoir and a respective well.

3. The method of claim 1, wherein the at least one supply duct is configured to establish fluid communication with the reservoir and a supply source.

4. The method of claim 2, further comprising:
   forming at least one growth channel in the substrate, wherein the at the least one well includes a first well and a second well, and wherein the at the least one growth channel includes a first growth channel and a second growth channel, and
   wherein the at least one growth channel is configured to establish fluid communication between the first well and the second well;
   forming at least one supply channel in the substrate, the at least one supply channel configured to establish fluid communication between one or both of a first supply duct among the at least one supply duct and the at least one well, and a first supply duct among the at least one supply duct and a second supply duct among the at least one supply duct; and
   forming at least one bridge channel in the substrate, the at least one bridge channel configured to establish fluid communication between the first growth channel and the second growth channel.

5. The method of claim 4, wherein forming the channel network further comprises forming at least one drain channel in fluid communication with the at least one growth channel and the at least one supply channel, the at least one drain channel configured to establish fluid communication with a waste receptacle.

6. The method of claim 4, further comprising forming at least one growth barrier disposed in at least one of the channels included in the channel network.

7. The method of claim 1, wherein forming the plurality of growth barriers comprises:

forming a first growth barrier in a first supply channel extending from a first supply duct to a first well;

forming a second growth barrier in a second supply channel extending from the first supply duct to a second well;

forming a third growth barrier in a third supply channel extending from the first supply duct to a second supply duct; and forming a fourth growth barrier in one of a fourth supply channel extending from the second supply duct to a third supply duct and a fourth supply channel extending from the first supply duct to the at least one drain channel.

8. The method of claim 1, wherein each of the channels define an internal area, and the growth barriers have a size less than the internal area to define spacings between a given barrier and sidewalls of the channels so as to partially block a given channel while still allowing fluid to flow therethrough.

9. The method of claim 1, further comprising forming at least one wiring structure embedded in the substrate.

* * * * *